United States Patent
Williams et al.

(10) Patent No.: US 11,864,983 B2
(45) Date of Patent: Jan. 9, 2024

(54) ABSORBENT ARTICLE WITH ELASTIC LAMINATE

(71) Applicant: The Procter & Gamble Company, Cincinnati, OH (US)

(72) Inventors: Tanner Laurie Williams, Loveland, OH (US); Urmish Popatlal Dalal, Milford, OH (US); Todd Douglas Lenser, Liberty Township, OH (US); Jeffry Rosiak, Loveland, OH (US); Miguel Angel Caballero, Cincinnati, OH (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 266 days.

(21) Appl. No.: 17/358,033

(22) Filed: Jun. 25, 2021

(65) Prior Publication Data

US 2021/0401638 A1    Dec. 30, 2021

Related U.S. Application Data

(60) Provisional application No. 63/043,902, filed on Jun. 25, 2020.

(51) Int. Cl.
*A61F 13/49* (2006.01)
*A61F 13/15* (2006.01)
*A61F 13/539* (2006.01)

(52) U.S. Cl.
CPC .. *A61F 13/49012* (2013.01); *A61F 13/15699* (2013.01); *A61F 13/4902* (2013.01); *A61F 13/539* (2013.01); *A61F 2013/15869* (2013.01); *A61F 2013/15926* (2013.01)

(58) Field of Classification Search
CPC .. A61F 2013/15869; A61F 2013/15926; A61F 13/49012
See application file for complete search history.

(56) References Cited

U.S. PATENT DOCUMENTS

| 10,568,776 B2 | 2/2020 | Lenser |
| 2018/0042787 A1* | 2/2018 | Lenser ............. A61F 13/49009 |
| 2018/0271716 A1 | 9/2018 | Dalal |

FOREIGN PATENT DOCUMENTS

WO    2018031837 A1    2/2018

OTHER PUBLICATIONS

15820M PCT Search Report and Written Opinion for PCT/US2021/039016 dated Oct. 22, 2021, 10 pages.

* cited by examiner

*Primary Examiner* — Carson Gross
(74) *Attorney, Agent, or Firm* — Daniel S. Albrecht; Wednesday G. Shipp

(57) ABSTRACT

A method for assembling elastic laminates includes the steps of stretching an elastic film at a spreader mechanism in the cross direction to a first elongation; advancing the elastic film from the spreader mechanism to an anvil, wherein the anvil comprises an active vacuum zone having a maximum width in the cross direction of Wv. The maximum width is divided into a first portion and a second portion, wherein the first portion is disposed in overlapping relationship with the engagement portion and inboard of the engagement portion in the cross direction and the first portion has a width in the cross direction of VZi and wherein the second portion has a width in the cross direction of VZo, and wherein a ratio of VZi is greater than to VZo is greater than 1.

18 Claims, 17 Drawing Sheets

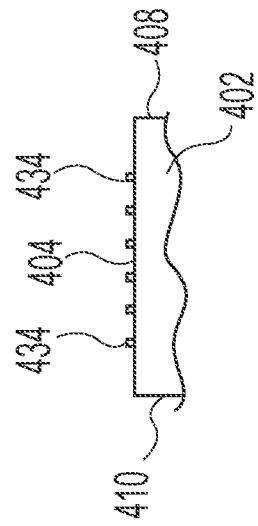
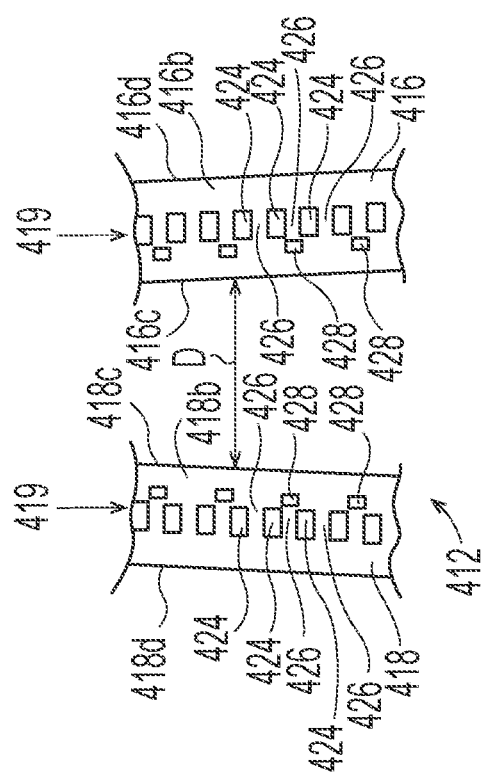
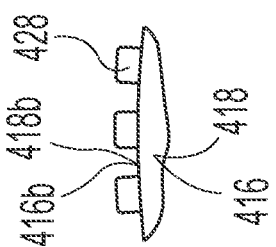

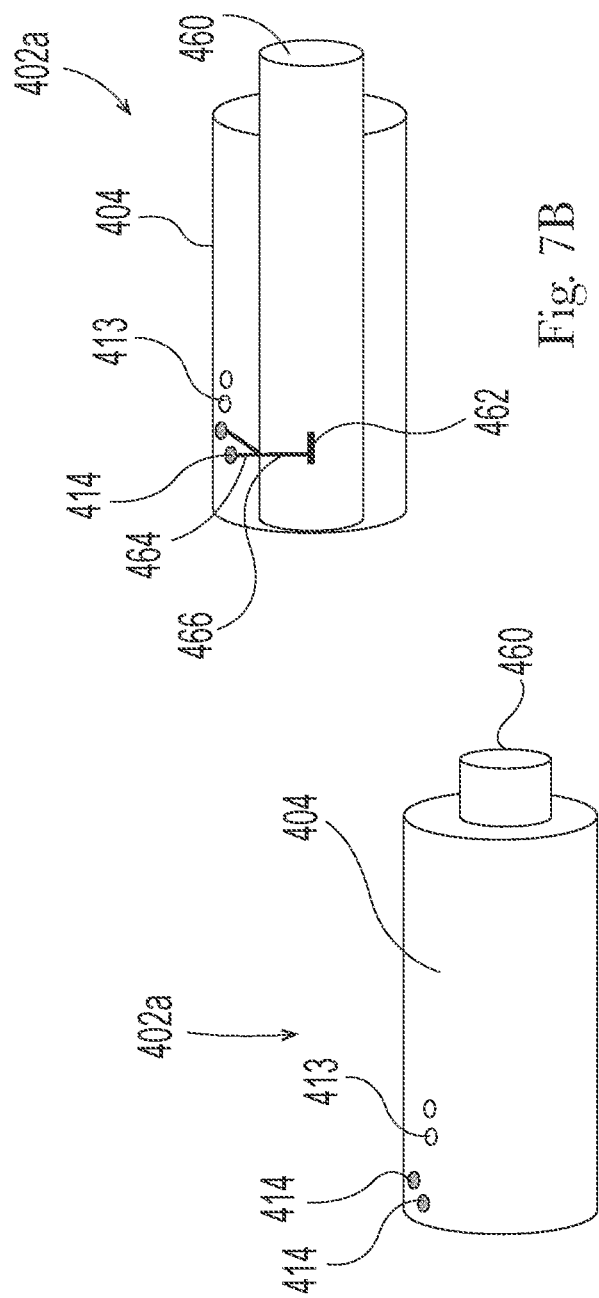

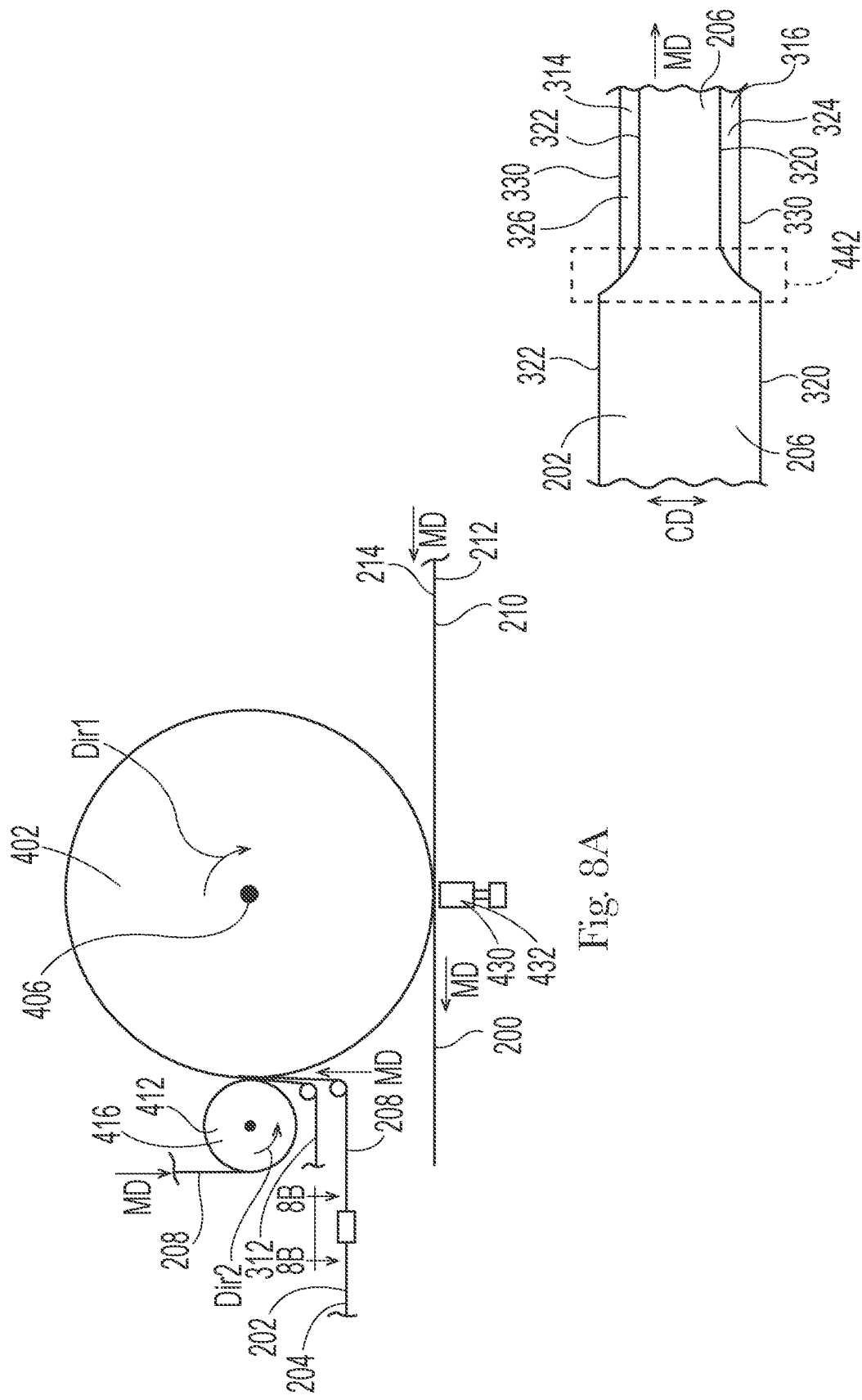

ABSORBENT ARTICLE WITH ELASTIC LAMINATE

FIELD OF THE INVENTION

The present invention relates to absorbent articles having stretchable laminates, such as stretchable ears or waistbands.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use extensible areas, such as stretch side panels (i.e., ears), within the article to help achieve a snug fit. When worn, the stretch ears extend the article about the hip and waist of the wearer to anchor the product in use while still allowing the wearer to move comfortably. A fastening system is typically joined to the ear to further secure the product about the wearer. Stretch ears are typically laminates of coverstock materials (such as nonwovens) and elastomeric materials. Similarly, waistbands may include stretchable laminates of nonwovens and elastomeric materials, and may help an absorbent article to fit snugly about the wearer's waist.

It is common to hold one or more edges of the elastomeric material during laminate making or activation. That is, although the material may be moving in the machine direction, an edge may be "held" close to or against an anvil or other surface for some time to help move the layers in a desired direction and/or to prevent layers from moving out of their desired position. For instance, in forming a gathered laminate, the elastomeric material may be stretched to a greater degree than a coverstock layer during lamination. Equipment may hold one or more edges of the elastomeric material against an anvil during stretch, resulting in said edges being unstretched. In order to hold the elastomeric material as desired, manufacturers must hold a fairly wide portion. However, the portions of the elastomeric material that are held may not provide extensibility to the final laminate. Stated differently, the unstretched elastomeric material in the areas where held do not contribute to the extensibility of the laminate to the same degree as the stretched portions. As such, manufacturers are not able to efficiently utilize the most expensive component of the laminate: elastomeric material.

Therefore, there is a need to reduce the area of unstretched elastomeric material in stretch laminates. There is also a need for laminates with smaller unstretched elastomeric material zones that still maintain integrity, breathability, and/or comfort. Moreover, there is a need for an efficient and cost-effective means of providing stretch laminates with smaller unstretched zones.

SUMMARY OF THE INVENTION

The invention comprises the features of the independent claims herein.

An absorbent article comprises a chassis comprises a topsheet, a backsheet, and an absorbent core disposed between the topsheet and backsheet; and an ear joined to the chassis. The ear comprises a laminate comprising a first nonwoven and second nonwoven and an elastomeric material sandwiched between said first and second nonwovens, wherein the laminate further comprises a plurality of ultrasonic bonds. The elastomeric material comprises a maximum dimension, Y, in a stretch direction, and the elastomeric material defines a primary region comprising an elastic region and one or more unstretched zones. The elastic region comprises a maximum dimension, X, in the stretch direction. The one or more unstretched zones comprises an aggregate maximum dimension in the stretch direction, Wd. The ratio of Wd to Y is 0.3 or less.

An absorbent article comprises a chassis comprising a topsheet, a backsheet, and an absorbent core disposed between the topsheet and backsheet; and an ear joined to the chassis. The ear comprises a laminate comprising a first nonwoven and second nonwoven and an elastomeric material sandwiched between said first and second nonwovens. The elastomeric material comprises a maximum dimension, Y, in a stretch direction, and the elastomeric material defines an elastic region, a first unstretched zone comprising a maximum dimension in the stretch direction, Wd1, and a second unstretched zone comprising a maximum dimension in the stretch direction, Wd2. A ratio of Wd2 to Wd1 is at least 2.

A method for assembling elastic laminates comprises the steps:
  providing a first substrate and a second substrate, the first substrate and the second substrate each comprising a first surface and an opposing second surface, and defining a width in a cross direction;
  wrapping the first surface of the first substrate onto an outer circumferential surface of an anvil;
  advancing an elastic film to a spreader mechanism, the spreader mechanism comprising an engagement portion and the elastic material;
  stretching the elastic material at the spreader mechanism in the cross direction to a first elongation;
  advancing the elastic material from the spreader mechanism to the anvil, wherein the anvil comprises an active vacuum zone having a maximum width in the cross direction of Wv, wherein the maximum width is divided into a first portion and a second portion, wherein the first portion is disposed in overlapping relationship with the engagement portion and inboard of the engagement portion in the cross direction and the first portion has a width in the cross direction of VZi and wherein the second portion has a width in the cross direction of VZo, and wherein VZi is greater than VZo;
  positioning the elastic material in contact with the second surface of the first substrate on the anvil;
  advancing the second substrate to position the first surface of the second substrate in contact with the elastic material and the second surface of the first substrate on the anvil; and
  ultrasonically bonding the first substrate together with the second substrate with the elastic material positioned between the first substrate and the second substrate.

BRIEF DESCRIPTION OF THE DRAWINGS

FIG. 4D is a detailed view of a spreader mechanism from FIG. 4C taken along line 4D-4D.

FIG. 4E is a detailed view of radially protruding nubs on an outer rim of a disk.

FIG. 4F is a detailed view of an anvil from FIG. 4B taken along line 4F-4F.

FIG. 7A is a schematic perspective view of an anvil in according to a nonlimiting embodiment of the present invention.

FIG. 7B is a schematic perspective view of the anvil of FIG. 7A with portions of the interior exposed to show a configurable tube according to a nonlimiting embodiment of the present invention.

FIG. 8A is a schematic side view of an apparatus operating to assemble elastic laminates.

FIG. 8B is a top side view of the first substrate advancing through a folding apparatus from FIG. 8A taken along line 8B-8B.

DETAILED DESCRIPTION OF THE INVENTION

Definitions

Figure 2:
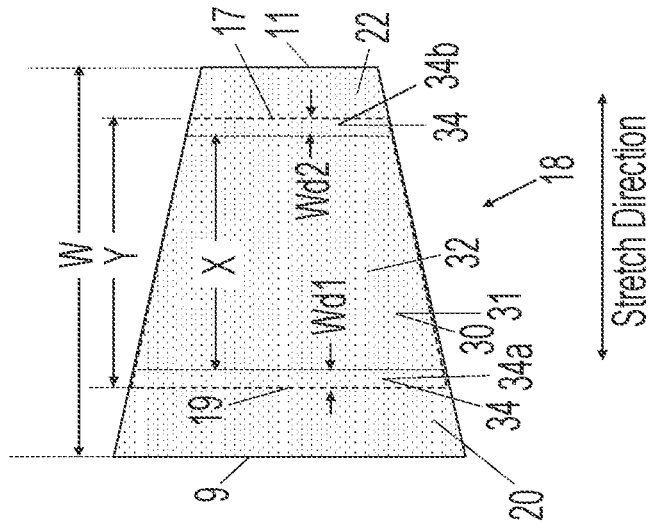
FIG. 2 is a plan view of an exemplary laminate according to a nonlimiting embodiment of the present invention.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Unstretched zone" means a portion of a gathered laminate comprising an elastomeric material that was substantially in a relaxed state during lamination. As discussed below, a gathered laminate is formed by extending an elastomeric material to a greater degree than another layer and bonding the elastomeric material to the other layer(s) while the elastomeric layer is extended. During such process, a portion of the elastomeric material is not extended, typically in order to hold the elastomeric layer in position on equipment. In the final laminate, these unextended portions together with the overlapping portions of other laminate layers form the unstretched zones.

"Elastic," "elastomeric," and "elastically extensible" mean the ability of material, or portion of the material, stretch by at least 50% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic. As used herein, a laminate is elastic if at least 20% of the area of the laminate meets the elastic definition herein. In this situation, the percent of area of the laminate is determined when the laminate is in a fully stretched state.

"Extensible" means the ability to stretch or elongate, without rupture or breakage, by at least 50% as per step 4(b) in the Hysteresis Test herein. As used herein, a laminate or substrate is extensible if at least 20% of the area of the laminate or substrate meets the extensible definition herein. In this situation, the percent of area of the laminate is determined when the laminate is in a fully stretched state. If a laminate does not meet the definition of elastic above, but does meet the definition of extensible provided in this paragraph, the laminate is an extensible laminate.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" means a sheet-like material wherein the length and width of the material far exceed the thickness of the material (e.g., 10×, 50×, or even 1000× or more). Films are typically liquid impermeable but may be configured to be breathable.

"Fully stretched" in reference to a corrugated laminate means when corrugations are substantially flattened by extending the laminate while making sure that the inelastic substrates of the laminate are not plastically deformed.

"Laminate" means two or more materials that are bonded to one another by any suitable method known in the art (e.g., adhesive bonding, thermal bonding, or high pressure bonding using non-heated or heated patterned roll).

"Inboard," with respect to a first feature of an article and its position relative a second feature or location on the article, means that the first feature lies closer to a respective axis of the article than the second feature or location, along a horizontal x-y plane approximately occupied by the article when laid out flat, extended to the full longitudinal and lateral dimensions of its component web materials against any contraction induced by any included pre-strained elastomeric material, on a horizontal surface. Laterally inboard means the first feature is closer to the longitudinal axis, and longitudinally inboard means the first feature is closer to the lateral axis. Conversely, "outboard," with respect to a first feature of an article and its position relative a second feature or location on the article, means that the first feature lies farther from the respective axis of the article than the second feature or location.

"Longitudinal" as used herein means the maximum linear dimension of the absorbent article in the x-y plane of the article. In an absorbent article as described herein, the longitudinal direction runs substantially perpendicular from a waist end edge to an opposing waist end edge when the absorbent article is in a flat out, uncontracted state, or from a waist end edge to the bottom of the crotch in a bifolded article. The longitudinal direction of any component of the absorbent article (e.g., an ear, a waistband) is determined when the component is joined to the article.

"Lateral" refers to a direction generally perpendicular to the longitudinal direction. In the absorbent article described herein, the lateral direction runs substantially parallel from a side edge to an opposing side edge.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" in reference to a laminate means at rest with substantially no external force acting on the laminate, other than gravity.

"Stretch direction" as used herein means the intended direction of elasticity in the final product. For example, a back ear in an absorbent article may be intended to be elastic in the lateral direction to conform around the waist of the wearer. The stretch direction of a laminate may be lateral and/or longitudinal. It is to be appreciated that a product may be elastic in multiple directions. In such cases, the stretch direction is the primary intended direction of elasticity in response to the expected application of force required for use.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Laminate

Figure 1:
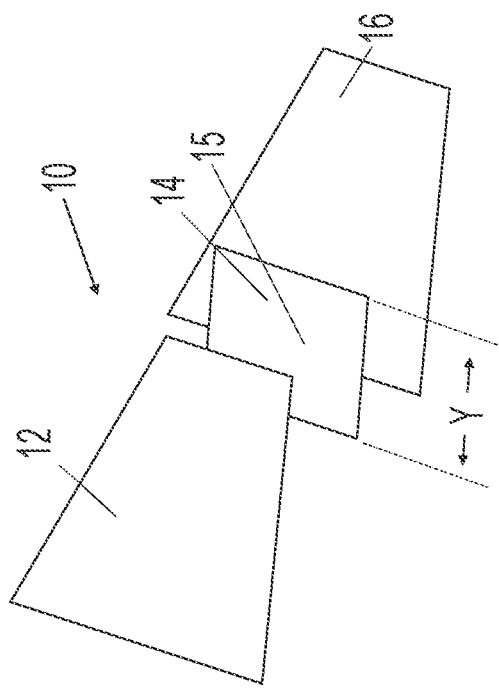
FIG. 1 is an exploded perspective view of an exemplary laminate according to a nonlimiting embodiment of the present invention.

As shown in FIG. 1, a laminate 10 comprises a first nonwoven 12 and an elastomeric layer 14. The laminate may comprise a second nonwoven 16, and the elastomeric layer 14 may be sandwiched between the first and second nonwoven. Additional layers may be included (e.g., additional nonwovens, inelastic materials, elastic or extensible materials, etc.). The laminate may be extensible. In certain embodiments, the laminate is elastomeric. Two or more laminate layers may be joined by a plurality of bonds 30 as shown in FIG. 2. The bonds comprise ultrasonic bonds 31, which may join nonwoven layers through the elastomeric layer. Ultrasonically bonded laminate may be formed by any suitable processes, including but not limited to those described in commonly assigned U.S. Patent App. Nos. 62/374,010, 62/419,515. The bonds may comprise heat bonds, pressure bonds or combinations thereof. The bonds may be any suitable shape or size. In some embodiments, bonds are non-circular. Additionally, or alternatively, bond may have longitudinal dimensions that are greater than their lateral dimensions or vice versa. An ear 130 and/or a waistband 180 of an absorbent article may comprise a laminate of the present invention.

Any suitable nonwoven may be used in the laminate 10. Suitable nonwovens may comprise a basis weight of at least about 8 gsm, or about 30 gsm or less, or about 22 gsm or less, or about 17 gsm or less, or from about 10 gsm to about 22 gsm, reciting for said range every 1 increment therein. Suitable nonwoven include but are not limited to spunbond, spunlaid, meltblown, spunmelt, spunlaced, solvent-spun, electrospun, carded, film fibrillated, melt-film fibrillated, air-laid, dry-laid, wet-laid staple fibers, hydro-entangled, and other nonwoven web materials formed in part or in whole of polymer fibers, as known in the art. In nonlimiting examples, a nonwoven comprises a meltblown layer. Additionally, or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens may be void of meltblown layers. In some embodiments, a nonwoven consists essentially of spunbond layers. In some nonlimiting examples, both the first and the second nonwoven comprises at least 2 spunbond layers, or 3 or more spunbond layers.

The nonwoven web may be formed predominately of polymeric fibers. In some examples, suitable nonwoven fiber materials may include, but are not limited to polymeric materials such as polyolefins, polyesters, polyamide, nylon, or specifically, polypropylene (PP), polyethylene (PE), polylactic acid (PLA), polyethylene terephthalate (PET) and/or blends thereof. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers. Further useful nonwovens, fiber compositions, formations of fibers and nonwovens and related methods are described in U.S. Pat. Nos. 6,645,569; 6,863,933; and 7,112,621; and in U.S. patent application Ser. Nos. 10/338,603; 10/338,610; and Ser. No. 13/005,237. The individual fibers of a nonwoven layer may be monocomponent or multicomponent (including bicomponent). The multicomponent fibers may be bicomponent, with differing polymeric components in, e.g., a core-and-sheath or side-by-side arrangement. The individual components may include polyolefins such as polypropylene or polyethylene, or their copolymers, or polyesters, thermoplastic polysaccharides or other biopolymers. Further, the nonwoven may include a blend of different fibers selected, for example from the types of polymeric fibers described above. In some examples, at least a portion of the fibers may exhibit a spiral curl which has a helical shape. According to one example, the fibers may include bicomponent fibers, which are individual fibers each including different materials, usually a first and a second polymeric material. It is believed that the use of side-by-side bi-component fibers is beneficial for imparting a spiral curl to the fibers. Examples of potentially suitable curled or "crimped" bicomponent fibers and nonwovens formed from them are described in U.S. Pat. Nos. 5,382,400; 5,418,045; 5,707,468; 6,454,989; 6,632,386; 5,622,772 and 7,291,239. For purposes herein, use of a nonwoven formed of crimped bicomponent or multicomponent fibers such as, for example, described in the patents and/or patent applications cited immediately above, may be desired as one or both nonwoven layers because they can feel particularly soft to the touch (for wearer comfort on the inside and aesthetically pleasing feel on the outside) and are generally quite pliable. In other nonlimiting examples, a nonwoven may be void of crimped fibers.

Where the laminate 10 comprises more than one nonwoven, the nonwovens may comprise the same basis weight or different basis weights. Likewise, the nonwovens may comprise the same layer configuration (e.g., SSS) or different layer configurations (e.g., SMS).

The elastomeric layer 14 comprises one or more elastomeric materials which provide elasticity to at least a portion of the layer 14. Nonlimiting examples of elastomeric materials include film (e.g., films derived from rubber and/or other polymeric materials, polyurethane films), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives (SIS, SBS, SEBS, SEEPS, SEPS, SIBS, etc.), polyesters, polyurethanes, polyether amides, polyolefins (homo, random, block, co-polymer, etc.), combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, TX), SEPTON (styrenic block copolymer; available from Kuraray America, Inc., New York, NY), VECTOR (styrenic block copolymer; available from TSRC Dexco Chemical Company, Houston, TX), ESTANE (polyurethane; available from Lubrizol, Inc., Ohio), PEBAX (polyether block amide; available from Arkema Chemicals, Philadelphia, PA), HYTREL (polyester; available from DuPont, Wilmington, DE), VISTAMAXX (homopolyolefins and random copolymers, and blends of random copolymers, available from EXXON Mobile, Spring, TX), VERSIFY (homopolyolefins and random copolymers, and blends of random copolymers, available from Dow Chemical Company, Midland, Michigan), and INFUSE (Block copolymer available from Dow Chemical Company).

In nonlimiting examples, the elastomeric layer 14 comprises a film 15. The film may comprise a single layer or multiple layers. The film may be extensible or may be elastic in the lateral direction and/or in the longitudinal direction. The film may be preactivated as disclosed, for example, in U.S. Pat. No. 9,533,067. In nonlimiting examples, the elastomeric layer comprises an Average $F200_{PS}$ of about 3 N/in to about 5 N/in, or about 3.7 N/in to about 4.3 N/in and/or an Average $F200_{FC}$ of about 1 N/in to about 2.75 N/in according to the Elastomeric Layer Hysteresis Test Method herein, reporting for each range every 0.1 N/in increment therein.

The elastomeric layer may be shorter in one or more dimensions of the laminate than the laminate itself. For example, the elastomeric layer may comprise a maximum dimension, Y, in the stretch direction and the laminate may comprise a maximum dimension, W, in the stretch direction. In various embodiments, the stretch direction is the lateral direction. The maximum dimensions are measured when the laminate is in the relaxed state. In nonlimiting examples, Y may be less than W, by at least about 10 mm. In certain embodiments, Y is at least about 20% of, or from about 25% to about 100%, or from about 35% to about 85%, or about 80% or less of W, reciting for each range every 5% increment therein. In various embodiments, the stretch direction is the lateral direction. Additionally, or alternatively, the elastomeric layer may have a dimension that is equal to one or more dimensions of the laminate. For example, the elastomeric layer may comprise substantially the same longitudinal length of the laminate throughout the lateral width of the laminate. In some embodiments, the elastomeric layer may have a basis weight of from about 5 to about 150 gsm, or from about 10 to about 100 gsm, or less than about 150 gsm, reciting for each range every 5 gsm increment therein.

Turning to FIG. 2, the laminate 10 may comprise a primary region 18, defined by the perimeter of the elastomeric material 14, and one or more inelastic regions 20, 22. The primary region 18 comprises an elastic region 32 and one or more unstretched zones 34. In the elastic region, the laminate is elastically extensible. In the unstretched zones, the laminate may not be elastic despite the presence of the elastomeric layer. In some embodiments, the area of the primary region comprises at least about 20% of, or from about 30% to about 100%, or about 80% or less of the total area of the laminate, reciting for said range every 5% increment therein. In the relaxed state, the elastic region 32 may comprise a maximum dimension, X, in the stretch direction. In nonlimiting examples, the ratio of X to Y is at least about 0.7, or about 0.75, or from about 0.5 to about 0.95, reciting for said range every 0.05 increment therein.

One or more unstretched zones 34 may comprise an aggregate maximum dimension in the stretch direction, Wd. The aggregate maximum dimension is the sum of the maximum dimensions in the stretch direction of individual unstretched zones, taken when the laminate is in the relaxed state, that do not overlap in the stretch direction. In some embodiments, the one or more unstretched zones includes a first unstretched zone 34a and a second unstretched zone 34b. The first unstretched zone may comprise a first maximum dimension in the stretch direction, Wd1, in the stretch direction, and the second unstretched zone may comprise a second maximum dimension in the stretch direction, Wd2. In the embodiment shown in FIG. 2, the aggregate maximum dimension, Wd, is the sum of Wd1 and Wd2. In nonlimiting examples, the elastic region is disposed between the first and second unstretched zones. For instance, as shown in FIG. 2, the first unstretched zone 34a is laterally inboard of the elastic region when the laminate is attached to the article, and the second unstretched zone 34b is laterally outboard of the elastic region. The maximum dimensions of the individual unstretched zones may be disposed in substantially the same position along a line perpendicular to the stretch direction (e.g., where the stretch direction is lateral, Wd1 and Wd2 may be disposed at the same longitudinal position).

The first maximum dimension, Wd1, may be the same as the second maximum dimension, Wd2. Alternatively, the first maximum dimension, Wd1, may be different than the second maximum dimension, Wd2. In nonlimiting examples, Wd2 is greater than Wd1. For instance, where an absorbent article ear comprises the laminate, the second unstretched zone may be wider in the lateral direction, permitting a fastening system to be more securely joined to the ear and to overlap the elastomeric material. Joining the fastening system to the ear in the primary region 18, particularly in the unstretched zone 34b, improves the overall strength of the ear/fastening system combination during use and/or application. Without being bound by theory, it is believed that breakage in ears formed from ultrasonically bonded laminates initially occurs in an inelastic region near the outboard edge 11 as the intact nonwoven resists the stretching of the elastomeric layer; and therefore, joining the fastening system in the unstretched zone reduces the stress on an inelastic portion of the ear. In nonlimiting examples, the ratio of Wd2 to Wd1 is at least about 3, or at least about 2, or at least about 1.5, or from about 1.25 to about 3, reciting for said range every 0.5 increment therein. By attaching the fastening system in the primary region, less reliance upon the shape of the back ear is necessary in providing suitable strength.

In various embodiments, Wd may be about 13 mm or less, or about 12 mm or less, or about 10 mm or less, or about 6 mm or less, or from about 2 mm to about 13 mm, or from about 3 mm to about 12 mm, or from about 5 mm to about 10 mm, reciting for each range every 1 mm increment therein. Additionally, or alternatively, Wd1 or Wd2 may be about 6.5 mm or less, or about 6 mm or less, or about 3 mm or less, or about 2 mm or less, from about 1 mm to about 6.75 mm, or from about 1.5 mm to about 6.5 mm, reciting for each range every 0.1 increment therein.

In nonlimiting examples, the ratio of Wd to Y is 0.45 or less, or 0.375 or less, or 0.27 or less, or 0.25 or less, or 0.2 or less, or from about 0.05 to about 0.45, or from about 0.1 to about 0.4, reciting for each range every 0.05 increment therein. Additionally, or alternatively, the ratio of Wd to X is 0.9 or less, or 0.4 or less, or 0.25 or less, or from about 0.05 to about 0.9, or from about 0.2 to about 0.4, reciting for each range every 0.05 increments therein.

The laminate may comprise an Angle Maximum Peak Force of at least about 12 N, or at least about 20 N, at least about 25 N, or at least about 30 N, or at least about 40 N, or at least about 45 N, or from about 12 N to about 75 N, or from about 20 N to about 70 N, or from about 30 N to 65 N or from about 35 N to about 45 N, reciting for each range every 1 N increment therein according to the Angle Maximum Peak Force Test Method herein. Additionally, or alternatively, the laminate may comprise an Extension at 1000 gm-force of at least about 30 mm, or at least about 40 mm, or from about 20 mm to about 60 mm, or from about 30 mm to about 50 mm, reciting for each range every 1 mm increment therein, according to the Ear Extension Test Method herein.

Importantly, the Angle Maximum Peak Force and/or the Extension can be achieved even with the smaller dimensioned unstretched zones described herein. Further, reducing the unstretched zone by as little as 2-3 mm on one edge of the elastomeric material may enable the elastic region to move inboard (e.g., laterally inboard on an absorbent article ear) and/or increase the overall dimension of the elastic region in the stretch direction. In embodiments where the laminate forms an absorbent article ear, the fastening system joined to the ear exerts tensile forces in the stretch direction when stretched for intended use. Reducing the unstretched zones may allow such tensile forces to be more evenly distributed over the elastomeric material, reducing sheer stresses and/or the tendency to buckle or rope (i.e., decrease in height in the direction perpendicular to the stretch direction), which in turn enhances fit and reduces skin bruising/marking. In addition, by improving tensile force distribution, lower basis weight elastomeric materials may be used. Further, positioning the elastic region inboard or outboard may shift the extension versus tensile force curve. A given extension could be achieved at lower or higher force than known configurations due to this shifting, allowing for more freedom in design.

Table 1 provides a comparison of known ear laminates and an inventive example.

TABLE 1

|  | Control | Inventive Example |
|---|---|---|
| Laminate Width (W) | 75 | 75 |
| Elastomeric Layer Width (Y) | 50 | 45 |
| Elastic Region Width (X) | 33 | 33 |
| Aggregate Unstretched Zone Width (Wd) | 17 | 12 |
| Ratio of Aggregate Unstretched Zone to Elastomeric Layer Width (Wd/Y) | 0.34 | 0.26 |
| Ratio of Aggregate Unstretched Zone to Elastic Region Width (Wd/X) | 0.52 | 0.36 |
| Angle Maximum Peak Force (N) | 63 N | 60 N |
| Extension (mm) | 43 mm | 41 mm |

As shown in FIG. 2, the laminate may further comprise one or more inelastic regions. In certain embodiments, the laminate 10 comprises a first inelastic region 20, which extends laterally outward from a first laminate edge 9 of the laminate and is adjacent to the primary region 18 at a first elastomeric material edge 17. The laminate may further include a second inelastic region 22, which may extend laterally inward from a second laminate edge 11 and may be adjacent to the primary region 18 at a second elastomeric material edge 19. The first and second inelastic regions may be made of the same material(s) or different materials.

Figure 3:
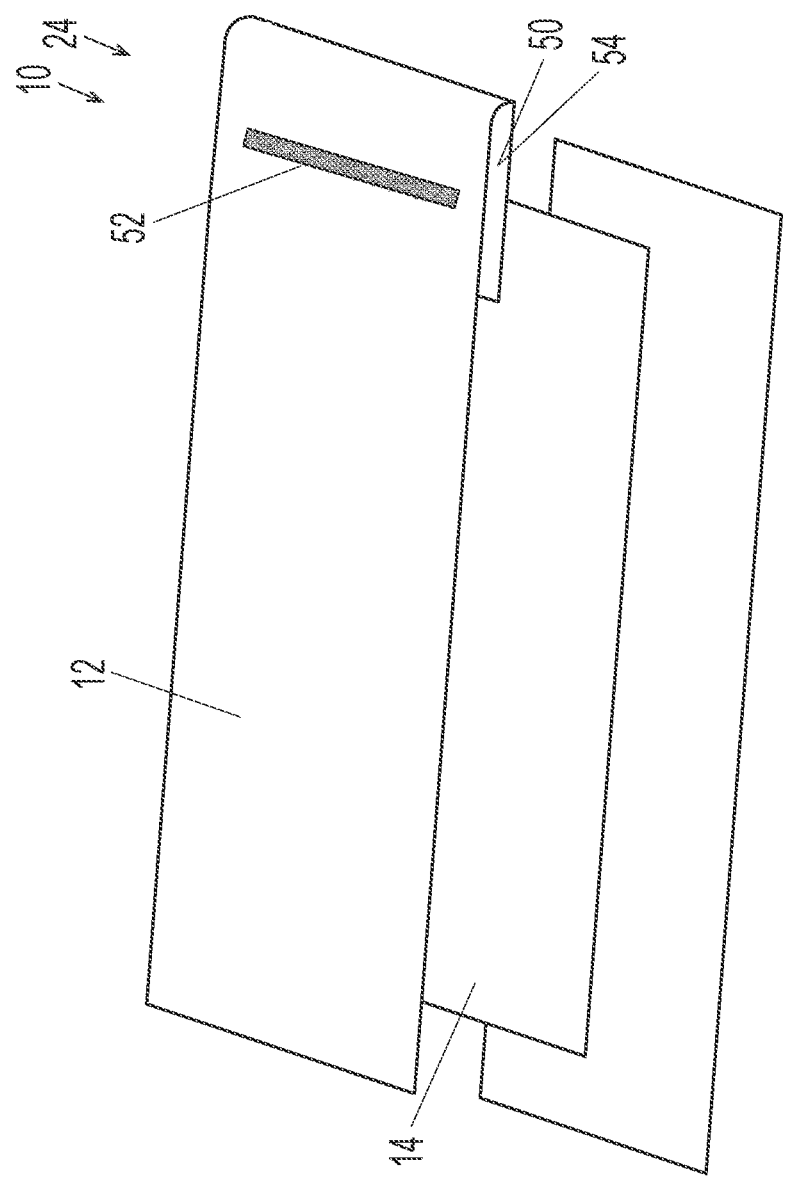
FIG. 3 is an exploded perspective view of an exemplary ear according to another nonlimiting embodiment of the present invention.

Turning to FIG. 3, the laminate 10 may further comprise a reinforcing feature 50 disposed between the elastomeric material and at least one of the nonwoven layers. The reinforcing feature aids in providing strength to the laminate. Nonlimiting examples of reinforcing features include additional bonding 52 such as adhesive, heat or pressure bonding; additional substrate layers 54 including separate material layers and/or folded material; and combinations thereof. Additional substrate layers 54 may comprise nonwovens, elastomeric materials or combinations thereof. An additional substrate layer 54 may comprise the same material as the first nonwoven, second nonwoven and/or elastomeric layer; or the additional substrate layer 54 may comprise a different material from any of the aforementioned layers.

The laminate 10 comprises a gathered laminate 24, wherein one of the layers (ideally elastic layer) is strained to a greater degree than a remaining layer during lamination. In this way, the less extensible layer (i.e., the nonwoven 12, 16) will form gathers when the laminate 24 is in a relaxed state. In some embodiments, at least a portion of the elastomeric layer is strained while the nonwoven(s) are in a relaxed state during lamination. The elastomeric layer may be stretched one or more directions. Corrugations then form in the nonwoven layer(s) when the subsequently formed laminate 24 is in a relaxed state. When making gathered laminates, the elastomeric layer is stretched in the stretch direction (i.e., the intended direction of stretch in the final product). The stretch direction may be lateral. In nonlimiting examples, the elastomeric layer is stretched in a direction corresponding with the lateral direction of the article. In other words, when the laminate is joined to the chassis subsequent to lamination, the laminate will be oriented such that the laminate is stretchable in the lateral direction of the article (i.e., the laminate is laterally-extensible).

In certain embodiments, the laminate may comprise an Breathability Value of at least about 1 $m^3/m^2/min$, or from about 1 $m^3/m^2/min$ to about 125 $m^3/m^2/min$, or from about 2 $m^3/m^2/min$ to about 50 $m^3/m^2/min$ according to the Air Permeability Test Method herein, reciting for each range every 1 $m^3/m^2/min$ increment therein.

In some embodiments, the laminate may be void of adhesive.

The laminate may include opacifying materials to reduce transparency through the laminate, particularly in the stretched state. Opacifiers, such as $TiO_2$, may be added to one or more of the laminate layers before, during or after formation of said layer(s). Additionally, or alternatively, the opacity of a precursor material may be enhanced through formulation, basis weight, number of layers, configuration of layers (e.g., SMS versus SS) or any combinations thereof. In nonlimiting examples, a nonwoven layer may be altered in the area where the elastomeric material is not present, thereby reducing transparency in said area. Additionally, or alternatively, laminate layers may be configured to match in color and/or opacity, which may result in an uniform appearance throughout the laminate even in areas where all laminate layers are not present.

Method of Making Laminates

Figure 4A:
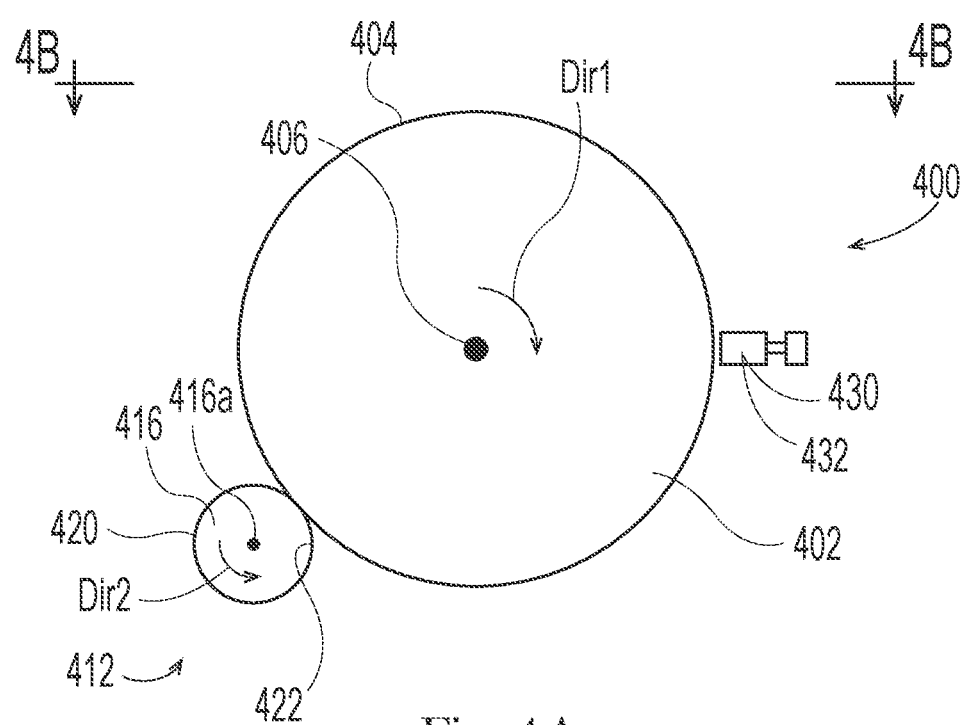
FIG. 4A is a schematic side view of an apparatus for assembling an elastic laminate according to a nonlimiting embodiment of the present invention.
Figure 4B:
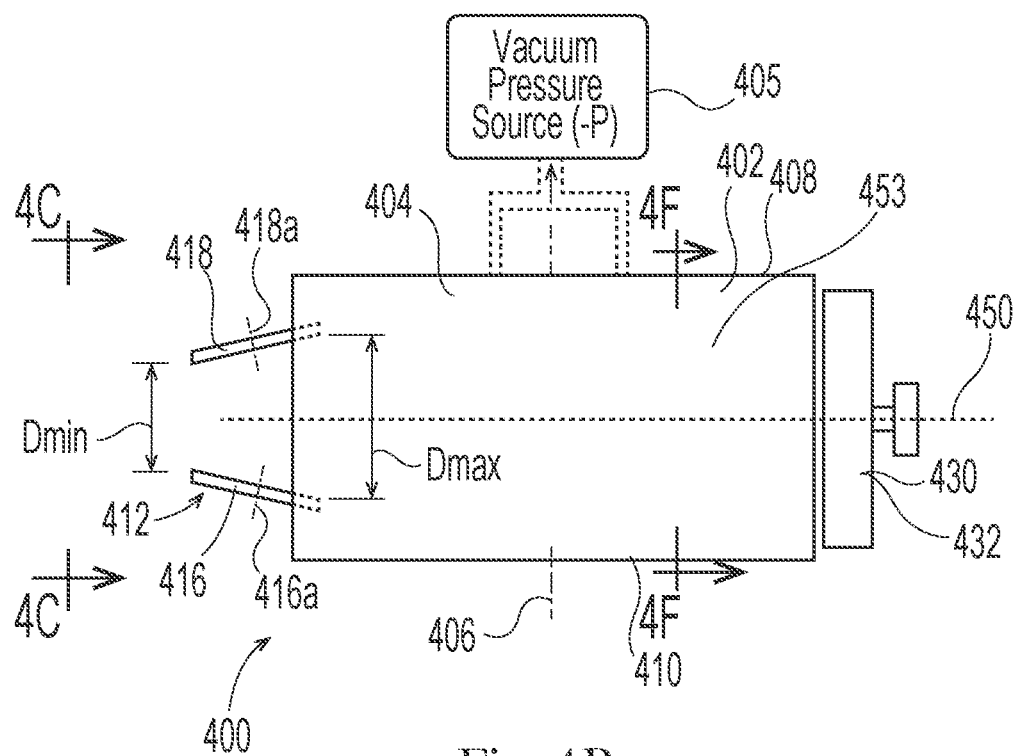
FIG. 4B is a top side view of the apparatus from FIG. 4A taken along line 4B-4B.
Figure 4C:
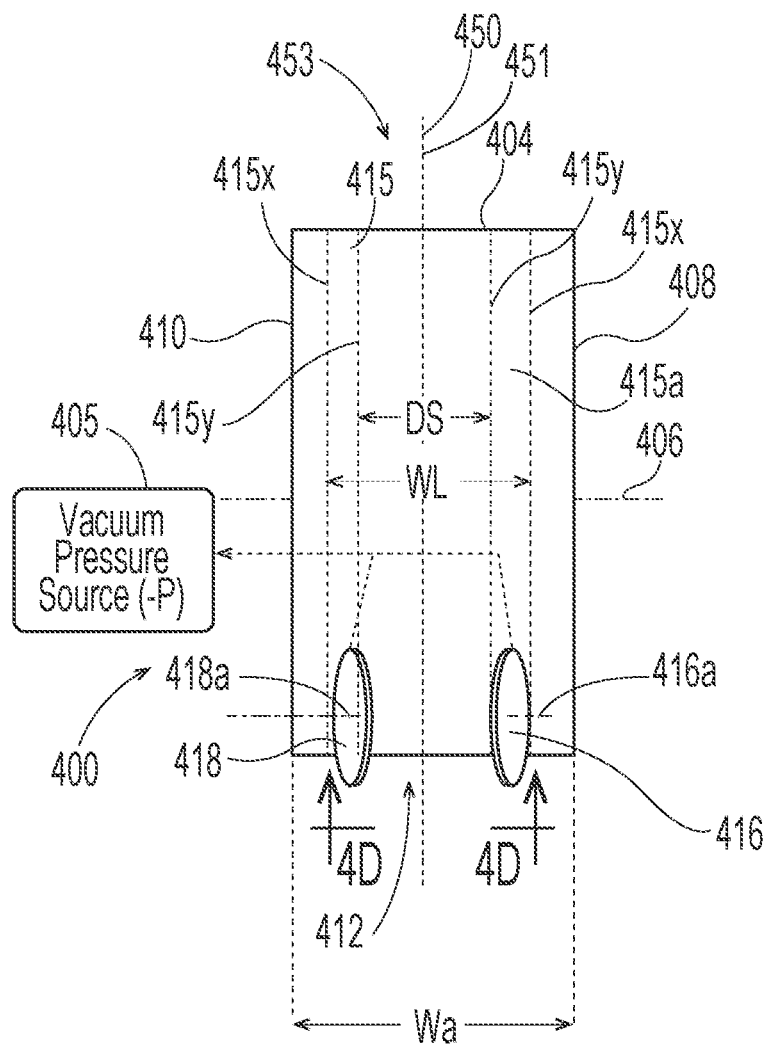
FIG. 4C is a left side view of the apparatus from FIG. 4B taken along line 4C-4C.

To help provide additional context to a subsequent discussion of the method configurations, the following provides a description of apparatuses that may be configured to operate in accordance with the methods disclosed herein. FIGS. 4A-4C show schematic side views of an apparatus 400 configured to assemble laminates of the present invention. As shown in FIGS. 4A-4C, the apparatus includes an anvil 402 having a cylindrically-shaped outer circumferential surface 404 and adapted to rotate in a first direction Dir1 about a first axis of rotation 406. Although the first direction Dir1 is depicted in FIG. 4A as clockwise, it is to be appreciated that the anvil 400 may be configured to rotate such that the first direction Dir1 is counterclockwise. As discussed in more detail below, substrates (e.g., nonwovens) and elastomeric materials may be combined on the rotating anvil 402 to form an elastic laminate. The anvil roll 402 has a maximum width in the cross direction, Wa, between a first side 408 and a second side 410. The anvil 402 may comprise a single lane 453 wherein only one laminate is produced at a time on the anvil 402, or multiple lanes 453 wherein two or more strips of elastomeric material (or strips of other laminate layer(s)) can be processed, each in their own lane, which may result in multiple laminates being formed in the same run as described for example in U.S. Pat. No. 10,568,775 to Lenser, et al.

As shown in FIG. 4B, the anvil 402, and more particularly, the outer circumferential surface 404 may also be fluidly connected with a vacuum pressure source 405. As such, vacuum air pressure may be used to help hold the substrates and elastic materials onto the outer circumferential surface 404 of the anvil 402 during operation. For example, with reference to FIGS. 4B-4C and 6A, the outer circumferential surface 404 of the anvil roll 402 may include a plurality of apertures 414 fluidly connected with the vacuum pressure source 405. In turn, the apertures 414 define an active vacuum zone 415, which may extend in the cross direction CD for a maximum width, Wv. For the purposes of clarity, dashed lines 415x, 415y are shown in FIG. 4C to represent example boundaries of the active vacuum zone 415. The maximum width, Wv, of the active vacuum zone may be less than the maximum CD width of the anvil, Wa. A lane on the anvil may comprise a maximum CD width, WL, extending between machine direction barriers or nubs extending along the anvil or extending the largest CD width of the stretched strip of material during processing, whichever is greater. The maximum width of the active vacuum zone, Wv, may be less than the maximum CD width of the lane, WL. The maximum width of the active vacuum zone, Wv, may be no more than about 20%, or about 15%, or about 10% of the maximum width of the lane, WL. In various embodiments, the active vacuum zone does not overlap the cross direction centerline 450 of the anvil and/or does not overlap the cross direction centerline 451 of one or more lanes 453. In this way, the active vacuum zone holds down the edges of the substrates and/or elastomeric material which may be sufficient to ensure the remaining portions (e.g., central portion) of the elastomeric materials and/or substrates are held down against the anvil. For clarity, although shown in FIGS. 4A-4C as coinciding, it is to be appreciated that the centerline 451 of a lane may not coincide with the centerline of an anvil 450, even when the anvil only includes one lane.

As shown in FIG. 4C for example, the anvil 402 may also include a second active vacuum zone 415a. The second active vacuum zone may comprise any of the features and dimensions disclosed with respect to active vacuum zone 415. The second active vacuum zone may be separated from the active vacuum zone 415 by a distance DS in the cross direction that may be at least about 10%, or at least about 25%, or at least about 50%, or from about 10% to about 70% of the maximum width of the lane, WL, reciting for said range every 5% increment therein. In nonlimiting examples, DS is from about 10 mm to about 60 mm, or from about 25 mm to about 40 mm, reciting for each range every 5 mm increment therein.

Figure 6A:
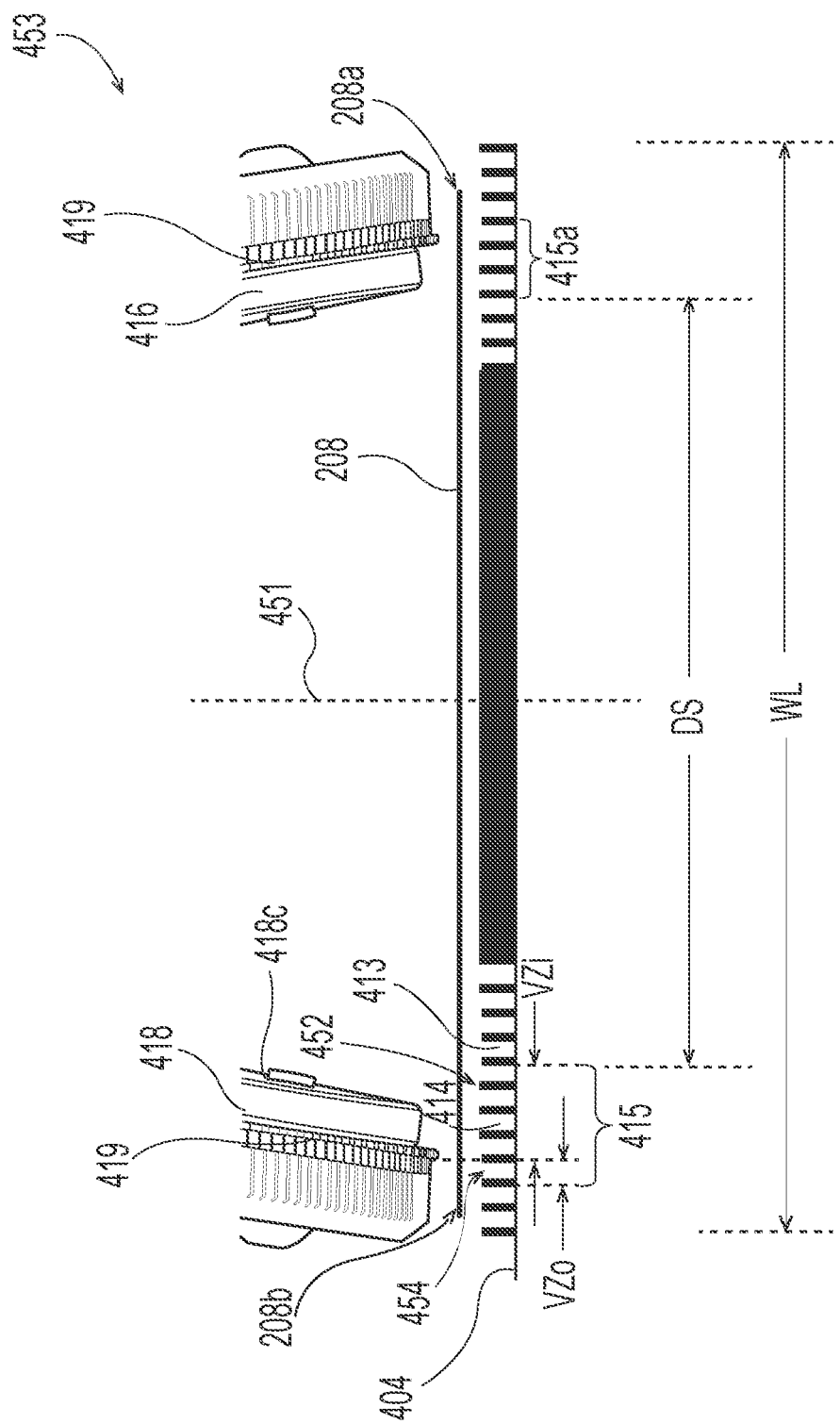
FIG. 6A is a schematic front view of an apparatus operating to stretch elastomeric material according to a nonlimiting embodiment of the present invention.
Figure 6B:
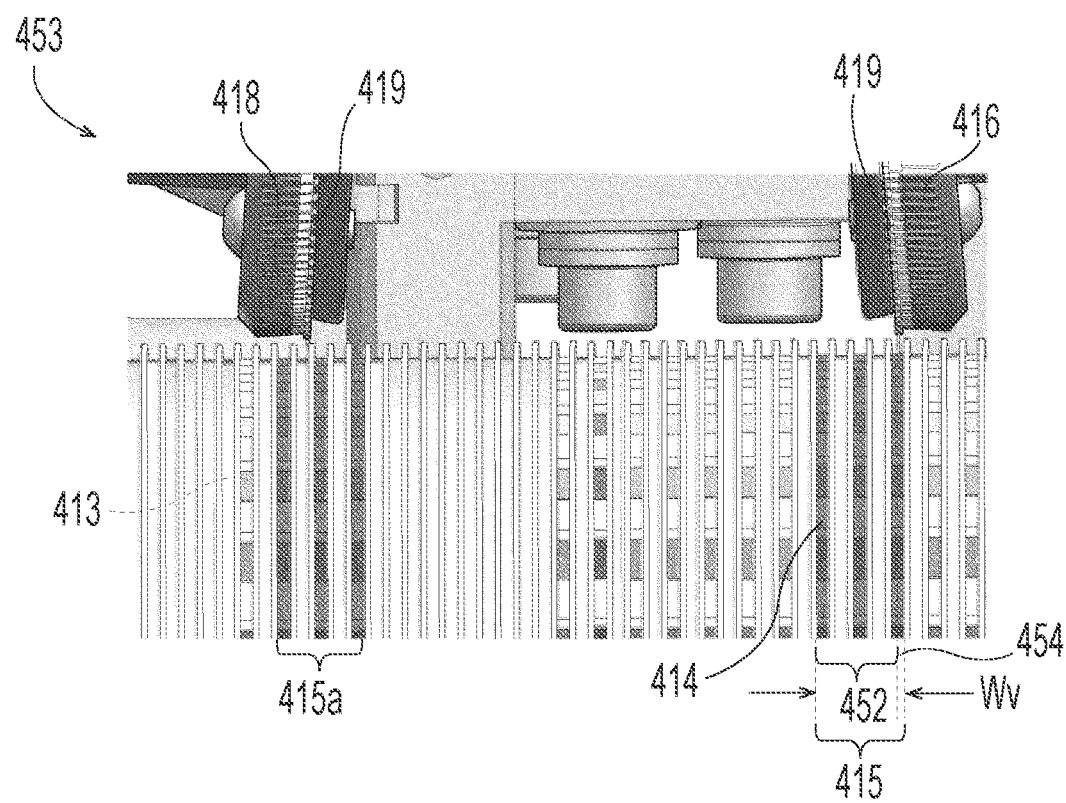
FIG. 6B is a schematic front view of an apparatus for use to stretch elastomeric material according to a nonlimiting embodiment of the present invention.

As can be seen in FIGS. 6A and 6B, the anvil may further comprise a plurality of inactive apertures 413. The inactive apertures are not fluidly connected to the vacuum pressure source and/or closed at the surface 404 during assembling in accordance with the present invention. The anvil may be configured to permit use of different apertures for different processes. As such, anvil may include both active apertures 414 and inactive apertures 413, with the active apertures 414 forming the active vacuum zone. Additionally, or alternatively, the anvil may comprise a machined anvil 402a configured to define active and inactive vacuum regions through the use of a configurable tube 460, as is discussed in more detail below with reference to FIGS. 7A-7C.

Returning to FIGS. 4A-4C, the elastomeric material 200 (which may the elastomeric material 14) may be activated via spreader mechanism 412 (or via other known activation processes such as ring-rolling). Elastomeric materials may include a base elastic layer and surface layers also known as skins. During activation, elastomeric materials may be extended or stretched to plastically deform the skins, such that they consolidate into micro-corrugations when viewed under a microscope. Such micro-corrugations may help reduce the skin contribution to the extension forces of the elastomeric material. With continued reference to FIGS. 4A-4C, the apparatus 400 may also include a spreader mechanism 412. As discussed in more detail below with reference to FIG. 5B, the spreader mechanism 412 may operate to activate the elastic material by stretching the elastic material in a cross direction from an initial CD width, Wi, to a first elongation, W1, during the elastic laminate assembly process. Optionally, the stretched elastic material may be consolidated to a second elongation, W2, wherein the second elongation may be less than the first elongation. Returning to FIG. 4A, the elastic material is advanced from the spreader mechanism 412 onto a substrate on the rotating anvil 402. It is to be appreciated that the apparatus 400 may include more than one spreader mechanism configured in various ways, such as disclosed for example in U.S. Patent Application Nos. 62/374,010; 62/406,025; and 62/419,515. In nonlimiting examples, an elastomeric material may be activated using a ring-rolling process as described in U.S. Pat. No. 10,568,776 to Lenser et al. It should be appreciated that two or more strips of elastomeric material may be stretched in individual lanes 453 with spreader mechanisms 412 for each lane. The spreader mechanisms may be disposed at different MD locations.

As shown in FIGS. 4A-4E, the spreader mechanism 412 may be configured with canted disks. For example, the spreader mechanism 412 may include a first disk 416 and a second disk 418, wherein the first disk 416 is displaced from the second disk 418 along the axis of rotation 406. The first disk 416 is adapted to rotate about an axis of rotation 416a and the second disk 418 is adapted to rotate about an axis of rotation 418a, wherein the first and second disks 416, 418 rotate in a second direction Dir2 that is opposite the first direction Dir1. Although the second direction Dir2 is depicted in FIG. 4A as counterclockwise, it is to be appreciated that the disks 416, 418 may be configured to rotate such that the second direction Dir2 is clockwise. In addition, the first disk 416 includes an outer rim 416b extending axially between an inner edge 416c and an outer edge 416d, and the second disk 418 includes an outer rim 418b extending axially between an inner edge 418c and an outer edge 418d.

As shown in FIGS. 4A-4D, the first disk 416 and the second disk 418 are canted relative to each other such that the outer rims 416b, 418b are separated from each other by a distance D that increases from a minimum distance Dmin at a first location 420 to a maximum distance Dmax at a second location 422. As discussed below, an elastic material, such as an elastic film, may be advanced in a machine direction onto the outer rims 416b, 418b during operation. Because the first and second disks 416, 418 are canted, rotation of the disks 416, 418 causes the rims 416b, 418b to pull on edge regions of the elastic material and activate the elastic material by stretching the elastic material in a cross direction CD. The disks 416, 418 may comprise an engagement portion 419 configured to help grip opposing edge regions of the elastic material during operation. For example, with particular reference to FIGS. 4D and 4E, the first disk 416 and the second disk 418 may each include a channel 424 extending radially inward from the rims 416b, 418b. In turn, the channels 424 may be fluidly connected with a vacuum pressure source 405. As such, vacuum air pressure may be used to help hold the elastic material onto the rims 416b, 418b during operation. The disks 416, 418 may also include support members 426 extending across the channels 424 to the help prevent the elastic material from being drawn into the channels 424 by the vacuum air pressure. As shown in FIGS. 4D and 4E, the disks 416, 418 may also include nubs 428 that protrude radially outward from the rims 416b, 418b. As such, the nubs 428 may also act to help prevent the edge regions of the elastic material from sliding along the rims 416b, 418b while stretching the elastic material. It is to be appreciated that additional nubs 428 may be positioned inboard or outboard of the channels 424. In addition, nubs 428 may also be positioned on the support members 426.

As mentioned above, stretched elastic materials and substrates are combined on the anvil 402. The combined substrates and elastic materials may then be bonded together on the anvil 402 to form elastic laminates. As shown in FIGS. 4A and 4B, the apparatus 400 may include one or more ultrasonic mechanisms 430 adjacent the anvil 402. It is to be appreciated that the ultrasonic mechanism 430 may include one or more horns 432 and may be configured to impart ultrasonic energy to the combined substrates and elastic materials on the anvil 402. As shown in FIG. 4F, the anvil roll 402 may include a plurality of pattern elements 434 extending radially outward from the outer circumferential surface 404 of the anvil 402. As such, the ultrasonic mechanism may apply energy to the horn 432 to create resonance of the horn at frequencies and amplitudes so the horn 432 vibrates rapidly in a direction generally perpendicular to the substrates and elastic materials being advanced past the horn 432 on the rotating anvil 402. Vibration of the horn(s) 432 generates heat to melt and bond the substrates and elastic material together in areas supported by the pattern elements 434 on the anvil 402. It is to be appreciated that aspects of the ultrasonic mechanisms may be configured in various ways, such as disclosed for example in U.S. Pat. Nos. 3,113,225; 3,562,041; 3,733,238; 6,036,796; 6,508,641; and 6,645,330. Multiple lanes may, in nonlimiting examples, each have their own ultrasonic mechanisms. In some configurations, the ultrasonic mechanism may be configured as a linear oscillating type sonotrode, such as for example, available from Herrmann Ultrasonic, Inc. In some configurations, the sonotrode may include a plurality of sonotrodes nested together in the cross direction CD.

The apparatus may operate in various ways to assemble laminates. Suitable spreader configurations are disclosed in U.S. Pat. No. 10,568,776 to Lenser et al.

Figure 5A:
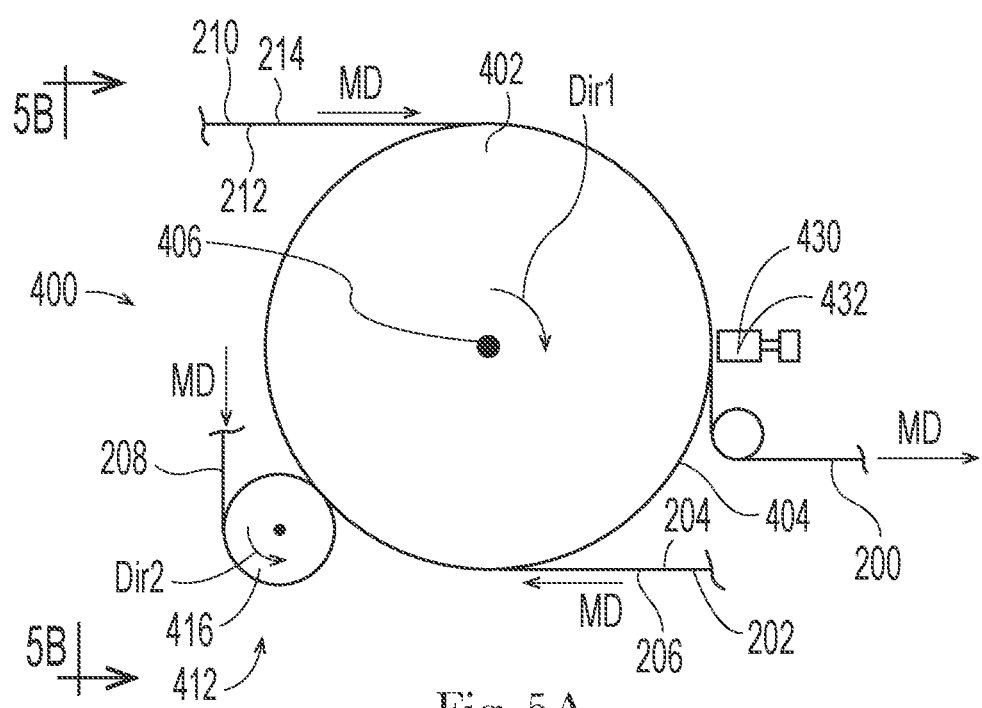
FIG. 5A is a schematic side view of an apparatus operating to assemble an elastic laminate according to a nonlimiting embodiment of the present invention.

In various embodiments illustrated in FIG. 5A, a first substrate 202 (which may be the first nonwoven 12) advances in a machine direction MD onto the rotating anvil 402. More particularly, the first substrate 202 includes a first surface 204 and an opposing second surface 206, and the first substrate 202 advances to wrap the first surface 204 onto the outer circumferential surface 404 of the rotating anvil 402. During the assembly process, the spreader mechanism 412 activates an elastomeric material 208 (e.g., the elastomeric layer 14, film 15) by stretching the elastic material 208 to a first elongation in the cross direction CD. The elastic material 208 is positioned into contact with the second surface 206 of the first substrate 202. In turn, the elastic laminate 200 (i.e., the laminate 10) may be formed by ultrasonically bonding the first substrate 202 and the elastic material 208 together with a second substrate 210 (e.g., the second nonwoven 16) on the anvil 402. More particularly, the second substrate 210 includes a first surface 212 and an opposing second surface 214, and the second substrate 210 advances to position the first surface 212 in contact with the elastic material 208 and the second surface 206 of the first substrate 202.

With continued reference to FIG. 5A, as the anvil 402 rotates, the first substrate 202, the elastic material 208, and the second substrate 210 are advanced between the outer circumferential surface 404 of the anvil 402 and the ultrasonic horn 432. In turn, the ultrasonic horn 432 bonds the first substrate 204, the stretched elastic material 208, and the second substrate 210 together to form the elastic laminate 200. The elastic laminate 200 may then advance from the anvil 402 to additional absorbent article assembly processes. In a relaxed state, a central region of the elastic material 208 is contracted (i.e., corrugated) in the cross direction CD. During the ultrasonic bonding process, it is to be appreciated that bonds imparted into the elastic laminate 200 from the ultrasonic horn 432 may correspond with patterns and/or shapes defined by the plurality of pattern elements 434 extending radially outward from the outer circumferential surface 404 of the anvil 402. It is to be appreciated that the elastic laminate 200 may include various portions of components bonded together in various ways and with differing or identical bond patterns. For example, the elastic material 208 may be bonded together with the first and/or second substrates 202, 210, and the first substrate 202 may be bonded directly to the second substrate 210 in areas of the elastic laminate 200. It is to be appreciated that the apparatus 400 may be adapted to create various types of bond configurations, such as disclosed, for example, in U.S. Pat. No. 6,572,595.

Figure 5B:
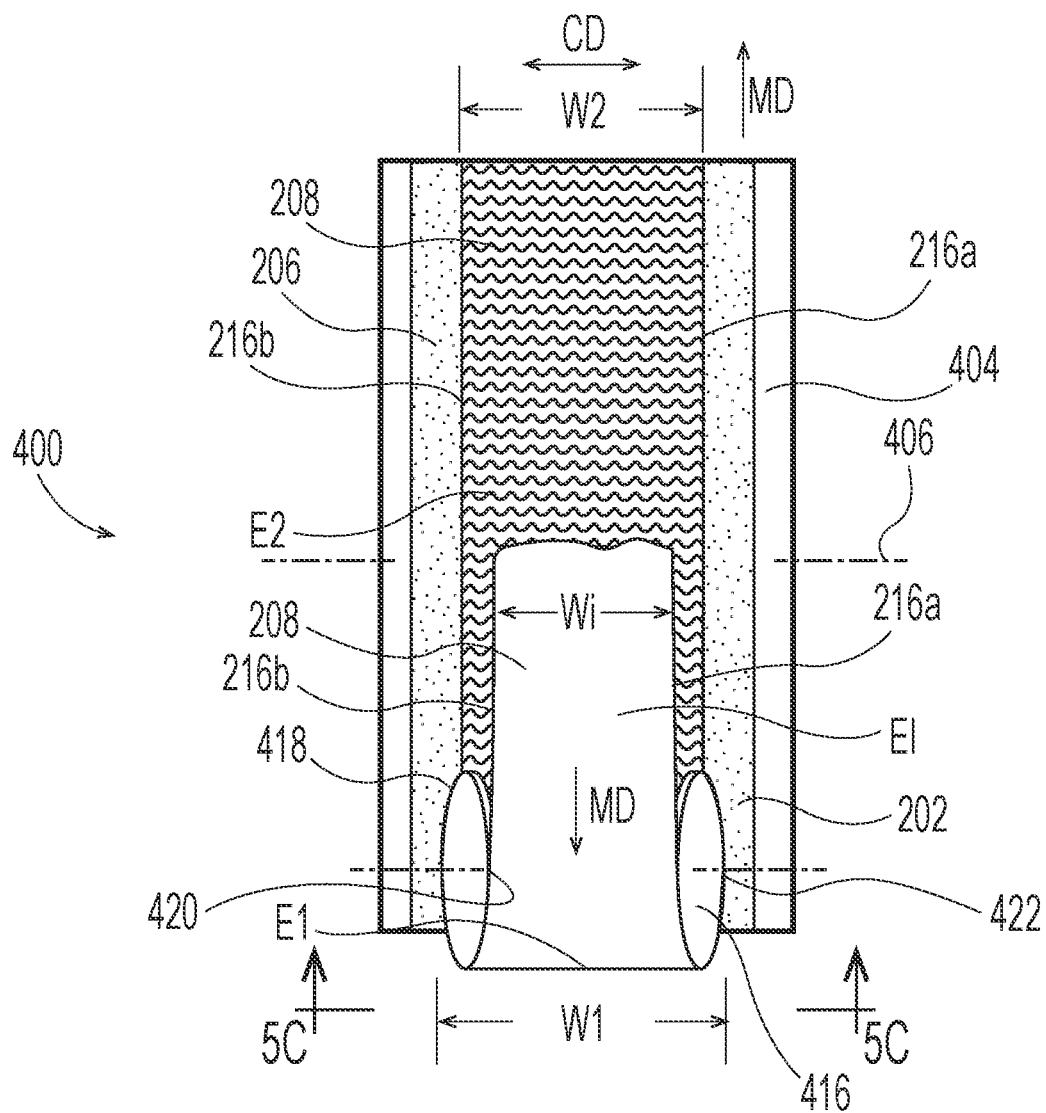
FIG. 5B is a left side view of the apparatus from FIG. 5A taken along line 5B-5B.
Figure 5C:
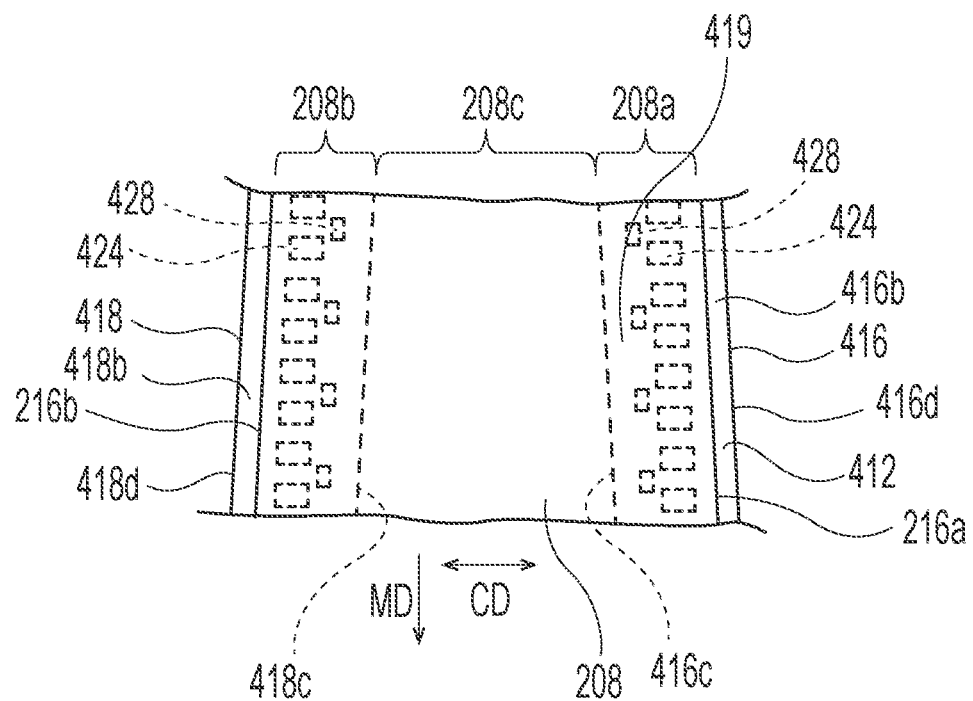
FIG. 5C is a top side view of the apparatus from FIG. 5B taken along line 5C-5C.

As shown in FIG. 5B, the spreader mechanism 412 activates the elastic material 208 by stretching the elastic material 208 from an initial width, Wi, having an initial elongation, Ei, to a first width, W1, having a first elongation, E1 in the cross direction CD. With particular reference to FIGS. 5A and 5C, the elastic material 208 includes a first edge 216a and a second edge 216b separated from the first edge 216a in the cross direction CD. In addition, the elastic material 208 includes a first edge region 208a adjacent the first edge 216a and a second edge region 208b adjacent the second edge 216b. The first edge region 208a is separated from the second edge region 208b in the cross direction CD by a central region 208c. As shown in FIGS. 5A and 5B, the elastic material 208 may define an initial width Wi in the cross direction CD between the first edge 216a and the second edge 216b upstream of the spreader mechanism 412. The elastic material 208 advances in a machine direction MD onto the spreader mechanism 412 at or downstream of the first location 420. It is to be appreciated that elastic material 208 may be at the initial width Wi in the cross direction CD while advancing onto the spreader mechanism 412. It is also to be appreciated that the elastic material 208 may be in a relaxed state upstream of the spreader mechanism 412.

As shown in FIGS. 5B-5C, the first edge region 208a of the elastic material 208 advances onto the outer rim 416b of the first disk 416 of the spreader mechanism 412, and the second edge region 208b advances onto the outer rim 418b of the second disk 418. The outer rims 416b, 418b of the first and second disks 416, 418 of the spreader mechanism 412 may include an engagement portion 419, such as include radially protruding nubs 428. Thus, as shown in FIG. 5C, the first edge region 208a of the elastic material 208 may be held in position on the outer rim 416b with the engagement portion. Similarly, the second edge region 208b of the elastic material 208 may be held in position on the outer rim 418b with the engagement portion.

Turning to FIGS. 6A-6B, which each depict a lane 453, the outer circumferential surface 404 of the anvil 402 may be fluidly connected with the vacuum source 405, and as such, vacuum air pressure may be applied to the first substrate 202 on the anvil 402. In addition, when the first substrate 202 is configured as a porous substrate, such as a nonwoven, vacuum air pressure may also be applied to the elastic material 208 on the anvil 402, and as such, may help maintain the stretched condition of the of the elastic material 208 while on the anvil 402. As further discussed above, the anvil includes one or more active vacuum zones 415, 415a.

An active vacuum zone comprises a maximum width, Wv in the cross direction. In various embodiments, the active vacuum is nominally into a first and second portion 452, 454. The first portion 452 extends from the area of overlap between the engagement portion 419 and the active vacuum and inboard towards the centerline 451 of the lane. The first portion comprises a width of VZi in the cross direction. The second portion 454 is the remaining width of the active vacuum zone. That is, the second portion is the portion of the maximum width that extends outboard of the engagement portion 419 (away from the centerline 451 of the lane). The second portion comprises a width of VZo in the cross direction. The width of the first portion VZi is greater than the width of the second portion VZo. The ratio of VZi to VZo is greater than 1. In nonlimiting examples, the ratio of VZi to VZo is greater than 2, or greater than 3, or greater than 5. In some embodiments, no more than one MD row of vacuum apertures is positioned outboard of the engagement portion of the spreader disks. In nonlimiting examples, the VZo is about 0.5 mm to about 3 mm, reciting for said range every 0.1 mm increment therein. In further nonlimiting examples, VZo is zero and there are is no active vacuum outboard the engagement portion. In these configurations, the width of a unstretched zone Wd1, Wd2 is less than the width of the second portion of the active vacuum VZo. Although VZo may be relatively small as described, the elastomeric material may still be pressed against the anvil due to lower static pressure of leakage air flow between an edge of the elastomeric material and the anvil, where said airflow may be high velocity. The edge of the elastomeric material may also seal against the anvil due to the vacuum static pressure of the source. The high speed leakage airflow may initiate the sealing via high static pressure.

Additionally, the first portion 452 may not extend to the centerline 451 of the lane and/or to the centerline 450 of the anvil. In nonlimiting examples, the first portion 452 is outboard of the inner edge 418c, 416c of a spreader disk (i.e., away from the centerline of anvil) at the innermost point of the inner edge of the respective spreader disk.

Referring to FIG. 6A, in use, the active vacuum zone 415 is positioned in overlapping relationship with one of the edge regions 208b, 208a of the elastomeric material. The second active vacuum zone 415a may be positioned in overlapping relationship with the other of the edge regions. The majority of the active vacuum width is disposed inboard of the respective elastomeric edge 216a, 216b.

Without being bound by theory, it is believed that the first portion provides sufficient operative normal force to hold the elastic material 208 against the anvil 402 to prevent slippage of the elastic material, while the second portion primarily ensures a flat laydown of the elastic material against the first substrate which may reduce wrinkles, edge misalignments, foldovers, and gathers. The second portion also aids the transfer of the elastomeric material off of the anvil.

Further to the above, the elastic material 208 must be tracked during processing to ensure continued control of the elastic material by the vacuum. A break in operative control of the elastic material may result in contraction of the elongated elastic material to a narrower width than desired prior to lamination, which may result in an unusable final product. Known methods and apparatuses did not consider that the CD width of the active vacuum region may be substantially wider and/or require higher differential pressure than the vacuum zone of a spreader, particularly for a tooth assisted canted disk spreader mechanism. Reducing width VZo may improve the robustness of the process by making the apparatus less sensitive to normal mistracking or misalignment of webs or material edges. The wrap angle around the plurality of teeth on the spreader disks, aided by a narrow region of a plurality of MD orientated vacuum holes may provide substantially more effective operational engagement of the spreader with the elastic material, helping to control the elastic material position against the anvil. Further still, by shifting the active vacuum inboard, the width of a unstretched zone can be reduced and less elastomeric material can be used, resulting in better, more efficient use of the elastomeric material.

Although the apparatus 400 may be configured to operate online as part of an absorbent article assembly process, it is to be appreciated that aspects of the apparatus 400 herein may be configured in various ways and may operate to assemble elastic laminates 200 from various types of material and/or components. For example, it is to be appreciated that in some configurations, the elastic laminate assembly operations may be performed separate to a final assembly process, such as for example, assembling the elastic laminates offline wherein the elastic laminates may be stored until needed for production. For example, elastic laminate assembly operations may be accomplished on discrete assembly lines, separately from converting lines that may be dedicated to manufacturing disposable absorbent articles. After assemblage on the discrete lines, the elastic laminates may be delivered to the absorbent article converting lines, such as in a form of rolls of continuous elastic laminates. It is to be appreciated that such rolls of continuous elastic laminates may be planetary wound or transversely wound. It is also appreciated that the elastic laminate assembly process may be done online during the article assembly process.

Turning to FIGS. 7A-7C, as noted above, the anvil may comprise a machined anvil 402a and may comprise a configurable tube 460 to define active and inactive vacuum regions. Known configurable anvils are formed from a plurality commutation disks. One or more of the commutation disks may be used to operatively connect a plenum of reduced static pressure with a surface of a substrate or elastic material. To avoid specific anvils for individual product sizes/designs, such anvils commonly supply vacuum to multiple commutation disks, with blocking elements used to determine which commutator disks are operationally active. A disadvantage of this scheme is the commutator disks may create void areas on the circumference of said anvil, the void areas being where no active vacuum port is present. Where an edge of an elastic material overlaps a void area, a tight seal may not be formed between the anvil and the elastic material and additional airflow may be drawn around said edge. Such additional airflow may act to reduce the differential static pressure between the surfaces of the elastic material (e.g. 204, 206), and thus lead to snap back and loss of desired extension of said elastic material. Further, leakage may occur from the transfer from the vacuum source to the vacuum ports.

In some embodiments, a block off device, integral with or discrete from the anvil outside surface 404, may be used to fill the void regions in commutator disks, which may enable a further reduction in unstretched zones because the vacuum may be more efficiently utilized and directed to the desired location of the elastic material.

Alternatively, the anvil may comprise a machined anvil 402a, fabricated from a solid metal blank. A substantial advantage of such fabrication is a reduction in air leakage around the edges of the film, thus enabling a better vacuum seal and/or a reduced plan area of resulting unstretched zones. With a machined anvil, a configurable tube 460 may be used rather than commutation disks. The tube 460 is removably disposed within the anvil and comprises ports 462 that are fluidly connected to a vacuum source. The ports 462 are also fluidly connected through radially connectors 466 to the outer circumference of the anvil. A plurality of blocking mechanisms 464 (e.g., valves) may be employed to direct vacuum pressure to active apertures 414 and thereby create active and/or inactive vacuum zones. Additionally, or alternatively, the tube 460 may be replaced with a second tube with an alternate configuration of vacuum porting to activate and inactivate alternate operative vacuum apertures in a circumference of the anvil. An advantage of this form of embodiment may be the elimination of void areas in the circumference of the anvil. Eliminating said void areas may reduce the leakage airflow around edges of the elastic material, enabling a higher differential pressure between the elastic material's surfaces 204, 206. Further, by supplying the vacuum within the roll, less leakage and thereby more efficient use of the vacuum can be expected. This mechanism is believed to enable an increased normal force and thus improved operative control of the extended elastic material on the anvil, even when the unstretched zone width is minimal or zero. Further still, as noted above, the use of one or more configurable tubes allows one anvil to be utilized for different production designs. For instance, vacuum ports on a configurable tube can be activated in different configurations or different tubes may be used with the same anvil. In this way, laminates may be formed in one lane and other laminates may be formed with multiple lanes on the same anvil. Likewise, laminates formed on the same anvil may different in dimensions, extensibility, configuration of unstretched zones and the like.

In one or more embodiments, one or more reinforcement materials 50 may be added to the laminate. Suitable methods for forming and incorporating reinforcement material layers are disclosed in U.S. Pat. No. 10,561,537 to Lenser et al. As shown in FIG. 8A, a first reinforcement layer 312 (e.g., a reinforcement substrate layer 54) may be advanced onto the second surface 206 of the first substrate 202. It is to be appreciated that the first reinforcement layer 312 may be formed in various ways. For example, the first reinforcement layer 312 is depicted as a discrete strip of material advanced onto the first substrate 202. The discrete strip of material may be a fastening tape. Additionally, or alternatively, additional reinforcement layers 314, 316 may also advance with the first substrate 202 onto the anvil roll 402. It is also to be appreciated that the first substrate 202 and/or the reinforcement layers 312, 314, 316 may also advance around guide rollers 144 such as shown in FIG. 8A. In nonlimiting examples shown in FIG. 8B, a substrate 202 may advance through a folding apparatus 442 that operates to fold portions of the substrate 202 to create one or more reinforcement layers 314, 316. The folding apparatus may operate to fold a first longitudinal edge 320 and/or a second longitudinal edge 322 of the substrate laterally inward in the cross direction, resulting in fold lines 330 and folded portions 324, 326 extending the machine direction and in the longitudinal direction in the final laminate as shown in FIG. 8B. The folded portions serve as reinforcement layers 314, 316. The second substrate 210 may be folded in the same manner to create one or more reinforcement layers. One or more reinforcement layers may be positioned between the second surface 206 of the first substrate and an edge region of the elastomeric material 208b, 208a. Additionally, or alternatively, one or more reinforcement layers may be positioned and/or between the first surface 212 of the second substrate 210 and an edge region 208b, 208a of the elastomeric material.

Article Comprising Laminate

Figure 9:
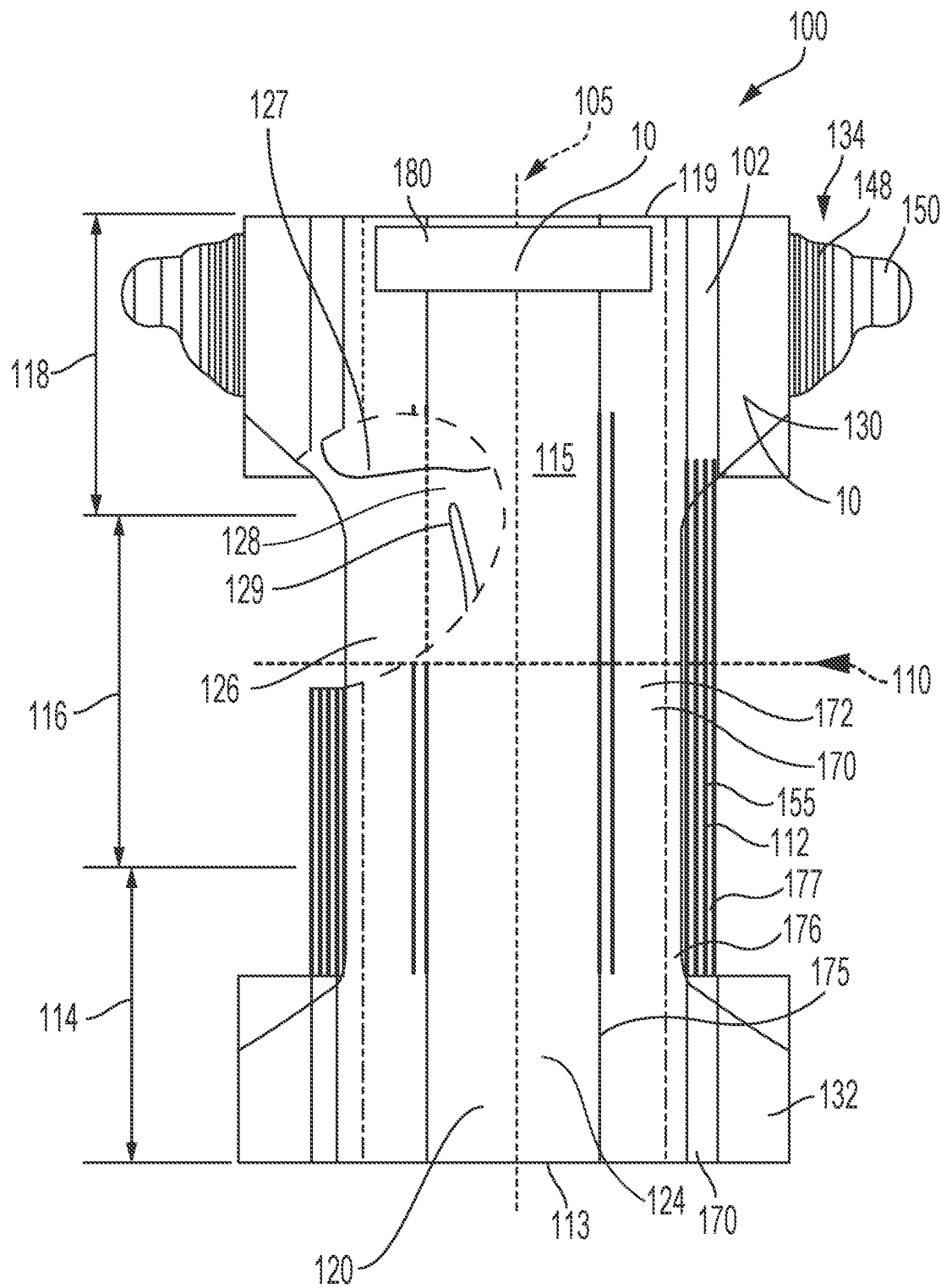
FIG. 9 is schematic plan view of an exemplary absorbent article according to a nonlimiting embodiment of the present invention. The absorbent article is shown in a flat, uncontracted state.

Turning to FIG. 9, a laminate 10 of the present invention may be incorporated into an absorbent article 100, such as a disposable absorbent article. The laminate may be attached to one or more layers of the chassis 120 by a chassis attachment bond 102. The chassis attachment bond may comprise ultrasonic bonds, adhesive bonds, mechanical bonds or combinations thereof.

FIG. 9 is a plan view of an exemplary, non-limiting embodiment of an absorbent article 100 of the present invention in a flat, uncontracted state. The body-facing surface 115 of the absorbent article 100 is facing the viewer. The absorbent article 100 includes a longitudinal centerline 105 and a lateral centerline 110.

The absorbent article 100 comprises a chassis 120. The absorbent article 100 and chassis 120 are shown to have a first waist region 114, a second waist region 118 opposed to the first waist region 114, and a crotch region 116 located between the first waist region 114 and the second waist region 118. The waist regions 114 and 118 generally comprise those portions of the absorbent article which, when worn, encircle the waist of the wearer. The waist regions 114 and 118 may include elastic members 155 such that they gather about the waist of the wearer to provide improved fit and containment. The crotch region 116 is the portion of the absorbent article which, when the absorbent article is worn, is generally positioned between the legs of the wearer.

The outer periphery of the chassis 120 is defined by longitudinal edges 112 and waist edges (first waist edge 113 in first waist region 114 and second waist edge 119 in second waist region 118). The chassis 120 may have opposing longitudinal edges 112 that are oriented generally parallel to the longitudinal centerline 105. However, for better fit, longitudinal edges 112 may be curved or angled to produce, for example, an "hourglass" shape article when viewed in a plan view as shown in FIG. 14. The chassis 120 may have opposing lateral edges 113, 119 (i.e., the first waist edge 113 and second waist edge 119) that are oriented generally parallel to the lateral centerline 110.

The chassis 120 may comprise a liquid permeable topsheet 124, a backsheet 126, and an absorbent core 128 between the topsheet 124 and the backsheet 126. The topsheet 124 may be joined to the core 128 and/or the backsheet 126. The backsheet 126 may be joined to the core 128 and/or the topsheet 124. It should be recognized that other structures, elements, or substrates may be positioned between the core 128 and the topsheet 124 and/or backsheet 126. In some embodiments, an acquisition-distribution system 127 is disposed between the topsheet 126 and the absorbent core 128.

In certain embodiments, the chassis 120 comprises the main structure of the absorbent article 100 with other features added to form the composite absorbent article structure. While the topsheet 124, the backsheet 126, and the absorbent core 128 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306. One or more masking layers or materials may be provided in the absorbent article. A masking layer may be a layer that provides a cushiony feel when the absorbent article is touched from the garment-facing surface or the wearer-facing surface. The masking layer may "mask" a grainy feel potentially caused by the absorbent material, such as superabsorbent polymers. The masking layer may "mask" bodily exudates from being visible when viewing the wearer-facing surface or the garment-facing surface of the absorbent article. The masking layer may have a basis weight in the range of about 15 gsm to about 50 gsm or about 15 gsm to about 40 gsm. The masking layer may comprise one or more nonwoven materials (e.g., a hydroentangled nonwoven material), foams, pulp layers, and/or other suitable materials. The masking layer may be the outer cover material of the backsheet. The masking layer may be the layer forming the garment-facing side or the wearer-facing side of the core. The masking layer may be a separate material positioned intermediate the garment-facing side of the core and the liquid impermeable backsheet.

Components of the disposable absorbent article can at least partially be comprised of bio-sourced content as described in U.S. Pat. Pub. Nos. 2007/0219521A1, 2011/0139658A1, 2011/0139657A1, 2011/0152812A1, and 2011/0139659A1. These components include, but are not limited to, topsheets, backsheet films, backsheet nonwovens, ears/ear laminates, leg gasketing systems, superabsorbent, acquisition layers, core wrap materials, adhesives, fastener systems, and landing zones. In at least one embodiment, a disposable absorbent article component comprises a bio-based content value from about 10% to about 100%, or from about 25% to about 75%, or from about 50% to about 60% using ASTM D6866-10, method B. In order to apply the methodology of ASTM D6866-10 to determine the bio-based content of any component, a representative sample of the component must be obtained for testing. In at least one embodiment, the disposable absorbent article component can be ground into particulates less than about 20 mesh using known grinding methods (e.g., WILEY® mill), and a representative sample of suitable mass taken from the randomly mixed particles.

The laminate 10 of the present invention may be form or be a portion of one or more components of the article, including but not limited to front ears, back ears and/or waist features.

Topsheet

The topsheet 124 is generally a portion of the absorbent article 100 that may be positioned at least in partial contact or close proximity to a wearer. The topsheet 124 is generally supple, soft feeling, and non-irritating to a wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet.

Absorbent Core

The absorbent core 128 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 129, wherein said channels are substantially free of absorbent particulate polymer material. The channels 129 may extend longitudinally or laterally. The absorbent core may further comprise two or more channels. The channels may be straight, curvilinear, angled or any workable combination thereof. In nonlimiting examples, two channels are symmetrically disposed about the longitudinal axis.

Exemplary absorbent structures for use as the absorbent core 28 are described in U.S. Pat. Nos. 4,610,678; 4,673, 402; 4,834,735; 4,888,231; 5,137,537; 5,147,345; 5,342, 338; 5,260,345; 5,387,207; 5,397,316, and U.S. patent application Ser. Nos. 13/491,642 and 15/232,901.

Backsheet

The backsheet 126 is generally positioned such that it may be at least a portion of the garment-facing surface of the absorbent article 100. Backsheet 126 may be designed to prevent the exudates absorbed by and contained within the absorbent article 100 from soiling articles that may contact the absorbent article 100, such as bed sheets and undergarments. In certain embodiments, the backsheet 126 is substantially water-impermeable. The backsheet may, for example, be or comprise a thin plastic film, such as a thermoplastic film having a thickness of about 0.012 mm to about 0.051 mm. Other suitable backsheet 126 materials may include breathable materials that permit vapors to escape from the absorbent article 100 while still preventing exudates from passing through the backsheet 126.

Backsheet 126 may also consist of more than one layer. The backsheet 126 may comprise an outer cover and an inner layer. The outer cover may be made of a soft, nonwoven material. The inner layer may be made of a substantially liquid-impermeable film, such as a polymeric film. The outer cover and an inner layer may be joined together by adhesive or any other suitable material or method. The outer cover material may comprise a bond pattern, apertures, and/or three-dimensional features. The outer cover may be a hydroentangled nonwoven material.

Ears/Fasteners

The absorbent article 100 may include one or more ears 130, including for example front ears 132 disposed in the first waist region and/or back ears 134 disposed in the second waist region. The ears 130 may be integral with the chassis or discrete elements joined to the chassis 120 at a chassis attachment bond 102, which may join one or more layers of the ear to the chassis. The ears 130 may be extensible or elastic. The ears 130 may be formed from one or more nonwoven webs, woven webs, knitted fabrics, polymeric and elastomeric films, apertured films, sponges, foams, scrims, or combinations and/or laminates of any the foregoing.

In some embodiments, the ear 130 may include elastomers, such that the ear is stretchable. In certain embodiments, the ears 130 may be formed of a stretch laminate such as a nonwoven/elastomeric material laminate or a nonwoven/elastomeric material/nonwoven laminate, which also results in the ear being stretchable. The ear 120 may be extensible in the lateral direction of the article. In some embodiments, the ear is elastic in the lateral direction. In further embodiments, the ear 130 may extend more in the lateral direction than in the longitudinal direction. Alternatively, the ear may extend more in the longitudinal direction than in the lateral direction. In certain nonlimiting examples, the ear may include one or more inelastic regions along with a separate elastic region.

In some embodiments, the ear comprises a laminate of one or more nonwovens and one or more elastic materials, such as the laminate 10 having any of the features or laminate layers described herein with respect to laminates of the present invention.

Any suitable nonwoven may be used in an ear 130. Suitable nonwovens may comprise a basis weight of at least about 8 gsm, or less than about 30 gsm, or about 17 gsm or less, or from about 10 gsm to about 17 gsm, reciting for said range every 1 increment therein. Typically, lower basis weight nonwovens reduce an ear's overall strength. However, the inventors have discovered ears designed according to the principles herein can obtain high strength despite lower basis weight nonwovens. Where the ear 130 comprises more than one nonwoven, the nonwovens may comprise the same basis weight or different basis weights. Likewise, the nonwovens may comprise the same layer structure or different layer structures. Further, a nonwoven in the ear may comprise the same or different features of nonwovens in the backsheet, topsheet, leg gasketing system and/or waist feature.

In various embodiments, the ear comprises an ultrasonically bonded ear. Ultrasonically bonded ears are disclosed for example in U.S. patent application Ser. No. 15/674,559. The ear may be a gathered laminate 24. Alternatively, the ear may be activated by processes disclosed in U.S. Pat. Pub. No. 2013/0082418 for example. In various embodiments, the ear comprises the laminate 10 of the present invention and may be formed by methods disclosed herein.

The ear may be joined to the chassis at a chassis attachment bond 102. In some nonlimiting examples, the chassis attachment bond is located in an inelastic region of the ear.

The absorbent article 100 may also include a fastening system 148. When fastened, the fastening system 148 interconnects the first waist region 116 and the rear waist region 118 resulting in a waist circumference that may encircle the wearer during wear of the absorbent article 100. The fastening system 148 may comprise a fastening elements 150 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 148 and/or the element 150 is foldable.

The fastening system 148 may be joined to any suitable portion of the article 100 by any suitable means. The fastening system may be joined to the ear between layers.

Leg Gasketing System

The absorbent article 100 may comprise a leg gasketing system 170 attached to the chassis 120, which may comprise one or more cuffs. The leg gasketing system may comprise a pair of barrier leg cuffs 172. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge joined directly or indirectly to the topsheet 124 and/or the backsheet 126 and a free terminal edge 175, which is intended to contact and form a seal with the wearer's skin. In some embodiments, the free terminal edge 175 comprises a folded edge. The barrier leg cuffs 172 extend at least partially between the front waist edge 113 and the rear waist edge 119 of the absorbent article on opposite sides of the longitudinal centerline 105 and are at least present in the crotch region. The barrier leg cuffs may be joined at the proximal edge with the chassis of the article by a bond which may be made by gluing, fusion bonding, or a combination of other suitable bonding processes.

The barrier leg cuffs may be integral with the topsheet 124 or the backsheet 126 or may be a separate material joined to the article's chassis. Each barrier leg cuff 172 may comprise one, two or more elastic elements 155 close to the free terminal edge 175 to provide a better seal.

In addition to the barrier leg cuffs 172, the article may comprise gasketing cuffs 176, which are joined to the chassis of the absorbent article, in particular to the topsheet 124 and/or the backsheet 126 and are placed externally relative to the barrier leg cuffs 172. The gasketing cuffs 176 may provide a better seal around the thighs of the wearer. A gasketing cuff may comprise a proximal edge and a free terminal edge 177. The free terminal edge 177 may comprise a folded edge. Each gasketing cuff may comprise one or more elastic elements 155 in the chassis of the absorbent article between the topsheet 124 and backsheet 126 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs. Suitable leg gasketing systems which may be part of the absorbent article are disclosed in U.S. Pat. App. No. 62/134, 622, 14/077,708; U.S. Pat. Nos. 8,939,957; 3,860,003; 7,435,243; 8,062,279.

Elastic Waist Feature

The absorbent article 100 may comprise at least one elastic waist feature 180 that helps to provide improved fit and containment, as shown in FIG. 9. The elastic waist feature 180 is generally intended to expand and contract to dynamically fit the wearer's waist. Elasticized waist features include waistbands, waist cuffs having pockets formed from a portion of the waist feature 180 that is unattached from the chassis 120, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 180 may be joined to the chassis 120 in the first waist region 114 and/or in the second waist region 118. The waist feature can be used in conjunction with the ear 130 to provide desirable stretch and flexibility for proper fit of the article on the wearer. The waist feature may be extensible or elastic in the lateral and/or longitudinal directions. The waist feature 180 may comprise a laminate 10 of the present invention and may be formed by methods disclosed herein.

Test Methods

Ear Extension Test Method

Extension of the ear is measured using a constant rate of extension tensile tester with computer interface such as MTS Alliance under Test Works 4 software (MTS Systems Corp., USA) fitted with a suitable load cell. The load cell should be selected to operate within 10% and 90% of its stated maximum load. All testing is performed in a conditioned room maintained at about 23° C.±2° C. and about 50%±2% relative humidity. Herein, width and length of the specimen are a lateral width and a longitudinal length. Precondition specimens at about 23° C.±2° C. and about 50%±2% relative humidity for 2 hours prior to testing.

Figure 11:
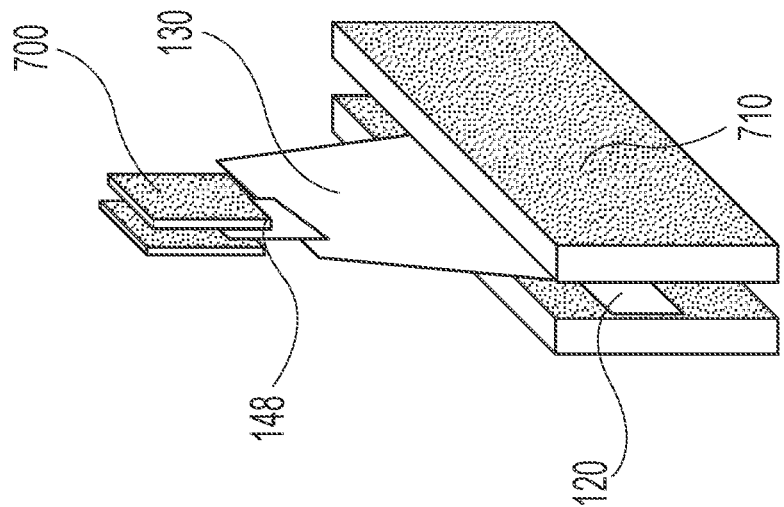
FIG. 11 is a schematic perspective view of grips suitable for use in the Ear Extension Test Method herein.

Flat grips or line grips should be used. FIG. 11 provides a schematic illustration of suitable top grips 700 and bottom grips 710. Grip faces can be serrated/diamond to hold the sample or can have rubber liner (1/32 in thick 60-70 A durometer neoprene rubber) on at least one of the two grip faces to hold the sample in place.

Figure 10:
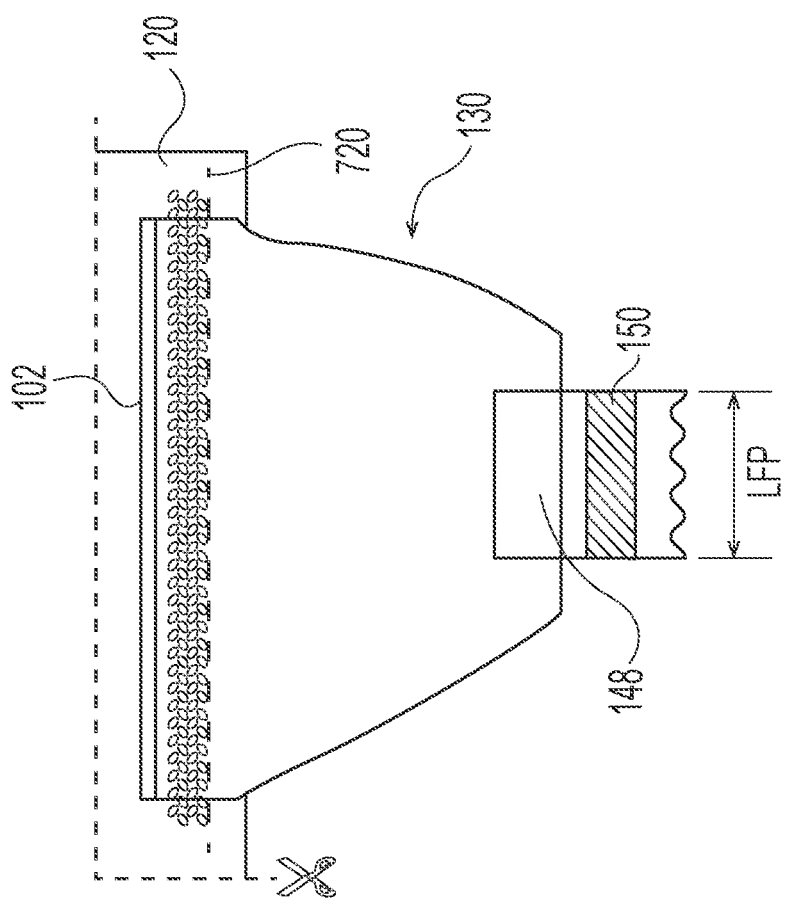
FIG. 10 is a schematic plan view of an exemplary ear in accordance with a nonlimiting embodiment of the present invention. The ear is shown in a relaxed state.

Ears are generally bonded to chassis via thermal or adhesive or similar bonding. To collect sample, product is placed flat on the cutting mat. Sample is collected by cutting product at approximately 20-30 mm below the ear's bottom edge as shown in FIG. 10. A left ear is separated from a right ear by cutting the cut sample in the middle.

Folded fastening systems (e.g., release tapes covering fastening elements) should be unfolded.

With reference to FIGS. 10-11:

1. Insert the outboard edge of the ear including fastener into the moving clamp (upper clamp) in the tester such that the clamp is centered in the tensile tester fixture and engage the clamp to grip the specimen. The clamp width selected is at least 25.4 mm, and preferably is not wider more than 1 inch than the length of the inboard edge of the fastener. The face of the clamp (once it grips the specimen) is aligned with the inboard edge of fastener to within 1 mm, the longitudinal midpoint of LFP is aligned with the center of the clamp, and the unclamped portion of the back ear hangs freely downward from the clamp.

2. Insert the inboard edge of the ear into the stationary clamp (lower clamp) in the tensile tester. The stationary clamp width is chosen such that no portion of the back ear extends beyond the width of the clamp. The face of the clamp (once it grips the specimen) is aligned with the junction line 720 to within 1 mm, and the specimen is oriented such that if a lateral line were drawn from the midpoint of LFP, it would extend vertically and align with the center of the fixture holding the lower clamp.

3. The lower grip location is adjusted so the specimen is gripped at the outboard edge of the chassis attachment bond 102. If the chassis attachment bond is curvilinear, the specimen is gripped at the outboard edge of the outermost bond.

4. Zero the crosshead location and load, and engage the lower clamp to grip the specimen.

5. Set the tensile tester to extend the specimen at a rate of 254 mm/minute and collect data at a frequency of at least 100 hz.

6. Initiate the test such that the tensile tester's clamp extends the specimen at the defined rate to break and data is collected into a data file.

7. Determine from the data the extension at 1000 gm-force load.

At least five (5) replicate specimens are run for each product example. The Average Extension at 1000 gm-force load and standard deviation for at least 4 specimens are recorded. If, standard deviation recorded is higher than 20%, a new set of five specimens is run.

Angle Maximum Peak Force Tensile Test Method

Figure 12A:
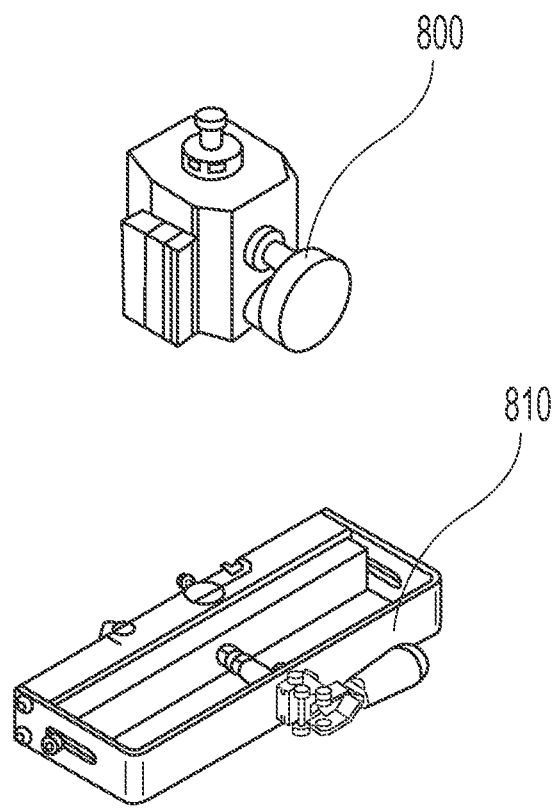
FIG. 12A is a schematic perspective view of grips suitable for use in the Angle Maximum Peak Force Tensile Test Method herein.

The Angle Maximum Peak Force Tensile Test is used to measure the strength of a specimen at a relatively high strain rate that represents product application. The method uses a suitable tensile tester that is equipped with actuator that is capable of speeds exceeding 1 m/s. Equipment model #AA-TS-ECH14-600 available from Allied Automation, Indianapolis can be used as the tensile tester. The tensile tester is fitted with a 50 lb. force transducer (such as 1500ASK-50). Grips shown in the FIG. 12A should be used to secure the specimens during tensile testing. Grip faces can be serrated as shown to hold the sample or can have rubber liner (1/32 in thick 60-70 A durometer neoprene rubber) on at least one of the two grip faces to hold the sample in place. Top grip 800 is fixed and is 38 mm wide to hold the fastener end of the product. The bottom grip 810 can travel and is wide enough to hold full width of the sample. The bottom grip fixture can also be rotated to 15 degrees to measure angled tensile strength.

(a) Tensile Test of Specimen from Absorbent Article

Ears are generally bonded to chassis via thermal or adhesive or similar bonding. To collect sample, product is placed flat on the cutting mat. Sample is collected by cutting product at approximately 20-30 mm below the ear's bottom edge as shown in the image. Left back ear is separated from the right ear by cutting in the middle as described in the Ear Extension Test Method herein. Folded fastening systems (e.g., release tapes covering fastening elements) should be unfolded.

Figure 12B:
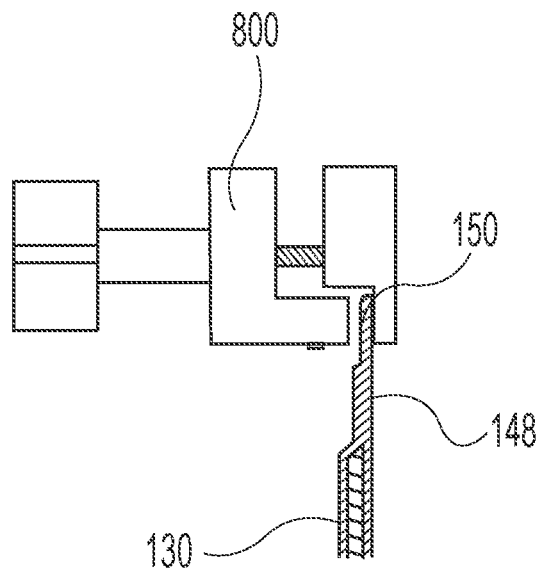
FIG. 12B is a schematic side view of a grip and ear as configured in the Angle Maximum Peak Force Tensile Test Method herein.
Figure 12C:
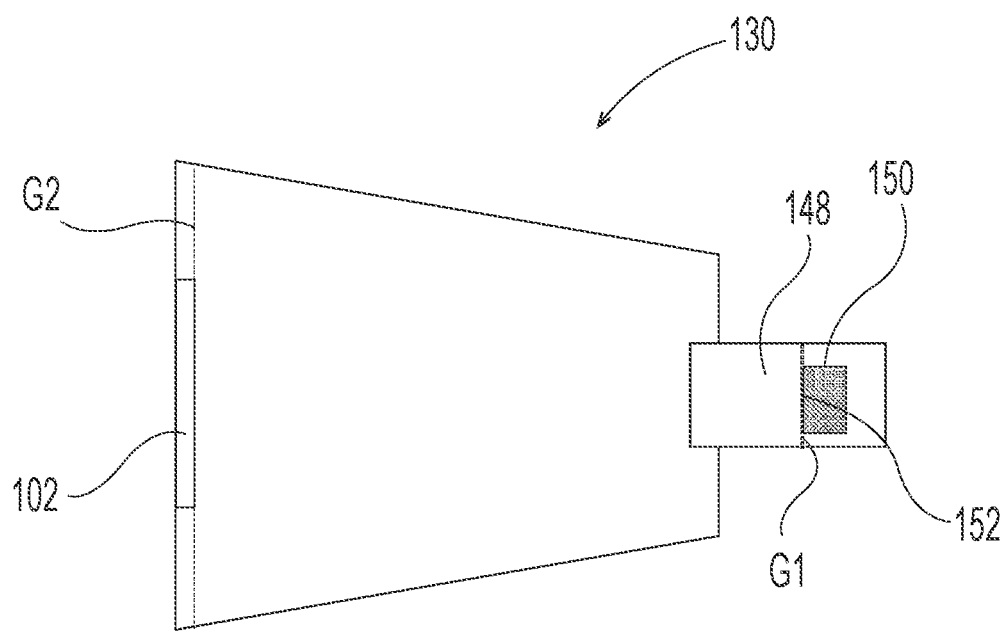
FIG. 12C is a schematic plan view of an exemplary ear in accordance with a nonlimiting embodiment of the present invention. The ear is shown in a relaxed state.

With reference to FIGS. 12B-12C, the specimen is clamped in the top grip at a first grip location G1 which is the inboard edge 152 of the fastener protruded engagement region 150. The grip line G1 is kept parallel to the longitudinal centerline of the product. If the fastener engagement region is angled, the specimen is gripped at the center of the region and grip line is kept parallel to the longitudinal centerline of the product at the center. The specimen is mounted and hung from the top grip. The opposing edge of the specimen is mounted in the bottom grip in relaxed condition. The bottom grip location G2 is adjusted so the specimen is gripped at the outboard edge of the chassis bond. If the chassis bond is curvilinear, the specimen is gripped at the outboard edge of the outermost bond. The bottom grip is wider than the length of the ear at the second grip location, G2. The top and bottom grips are parallel to each other. Once the sample is mounted, bottom grip is moved towards the top grip to put slack in the material. At this point, bottom grip with sample held in the grip is rotated 15 degrees to make angled measurement.

The specimen is tested as follows: The vertical distance (perpendicular to the grip line) from the first grip location, G1, to second grip location, G2, is measured to 0.1 mm using ruler and is used as gage length for the test. The specimen is tested at a test speed that provides 4 to 10 sec-1 strain rates for the gage length selected for the specimen. Test speed in mm/second is calculated by multiplying 4 to 10 sec-1 by the gage length in mm. For example, 125 mm gage length sample tested at 4 sec-1 strain rate will need 500 mm/sec test speed. On the other hand, 50 mm gage length sample tested at 10 sec-1 strain rate will also need 500 mm/sec test speed.

Each specimen is pulled to break. During testing, one of the grips (grip with tapes) is kept stationary and the opposing grip is moved. The force and actuator displacement data generated during the test are recorded at data acquisition frequency at minimum 1 kHz. The resulting load data may be expressed as load at break in Newton. Total of five (5) replicate specimens are run for example. The maximum peak force and standard deviation of at least 4 specimens are recorded as the Angled Maximum Peak Force. If, standard deviation recorded is higher than 10%, a new set of five specimens is run.

Basis Weight Test Method

Each specimen is weighed to within ±0.1 milligram using a digital balance. Specimen length and width are measured using digital Vernier calipers or equivalent to within ±0.1 mm. All testing is conducted at 22±2° C. and 50±10% relative humidity. Basis weight is calculated using equation below.

$$\text{Basis Weight}\left(\frac{g}{m^2}\right) = \frac{(\text{Weight of the specimen in grams})}{(\text{Length of the specimen in meter})(\text{Width of the specimen in meter})}$$

For calculating the basis weight of a substrate, a total 8 rectilinear specimens at least 10 mm×25 mm are used.

The average basis weight and standard deviation are recorded.

Hysteresis Test Method

This set-up applies to both General Hysteresis test and Elastomeric Layer Hysteresis test. A suitable tensile tester interfaced with a computer such as MTS model Alliance RT/1 with TestWorks 4® software or equivalent is used. The tensile tester is located in a temperature-controlled room at 22° C.±2° C. and 50±10% relative humidity. The instrument is calibrated according to the manufacturer's instructions. The data acquisition rate is set to at least 50 Hertz. The grips used for the test are wider than the sample. Grips having 2 inch (50.8 mm) width may be used. The grips are air actuated grips designed to concentrate the entire gripping force along a single line perpendicular to the direction of testing stress having one flat surface and an opposing face from which protrudes a half round (radius=6 mm—e.g. part number: 56-163-827 from MTS Systems Corp.) or equivalent grips—to minimize slippage of the sample. The load cell is selected so that the forces measured are between 10% and 90% of the capacity of the load cell or the load range used. The load reading on the instrument is zeroed to account for the mass of the fixture and grips.

The specimen is mounted into the grips in a manner such that there is no slack and the load measured is between 0.00 N and 0.02 N. The specimen basis weight is measured as per the basis weight method above. The specimen is mounted in the center of the grips, such that the specimen direction of stretching is parallel to the applied tensile stress.

General Hysteresis Test:
1. The specimen is cut with a dimension of 10 mm in the intended stretch direction of the sample X 25.4 mm in the direction perpendicular to the intended stretch direction of the sample. A specimen is collected from either an inelastic region or from an elastic region.
2. Set the distance between the grips (gauge length) at 7 mm.
3. Secure the specimen with intended stretch direction aligned with MTS strain direction with minimum slack as described above.
4.
   a. Pre-load step: Set the slack preload at 5 gram/force This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.
   b. First cycle loading: Pull the specimen to the 50% strain at a constant cross head speed of 70 mm/min. Report the stretched specimen length between the grips as $l_{max}$.
   c. First cycle unloading: Hold the specimen at the 50% strain for 30 seconds and then return the crosshead to its starting position (0% strain or initial sample length, $l_{ini}$) at a constant cross head speed of 70 mm/min. Hold the specimen in the unstrained state for 1 minute.
   d. Second cycle loading: Pull the specimen to the 50% strain at a constant cross head speed of 70 mm/min. Report the stretched specimen length between the grips at 7 gram-force as $l_{ext}$.
   e. Second cycle unload: Next, hold the specimen at the 50% strain for 30 seconds and then return the crosshead to its starting position (i.e. 0% strain) at a constant cross head speed of 70 mm/min.

A computer data system records the force exerted on the sample during the test as a function of applied strain. Report length to the nearest 0.001 mm. From the resulting data generated, the % Set is calculated using following equation.

% Set, which is defined as $(l_{ext}-l_{ini})/(l_{max}-l_{ini})*100\%$ to the nearest 0.01%.

The testing is repeated for at least 3 separate samples and the average and standard deviation reported.

Elastomeric Layer Hysteresis Test:
1. The specimen is cut with a dimension of at least 32 mm in the intended stretch direction of the sample X 25.4 mm (1 in) in the direction perpendicular to the intended stretch direction of the sample.
2. Set the distance between the grips (gauge length) at 25.4 mm (1 in).
3. Secure the specimen with intended stretch direction aligned with MTS strain direction with minimum slack as described above.
4.
   a. Pre-load step: Set the slack preload at 5 gram/force This means that the data collection starts when the slack is removed (at a constant crosshead speed of 13 mm/min) with a force of 5 gram force. Strain is calculated based on the adjusted gauge length ($l_{ini-ps}$), which is the length of the specimen in between the grips of the tensile tester at a force of 5 gram force. This adjusted gauge length is taken as the initial specimen length, and it corresponds to a strain of 0%. Percent strain during pre-strain test is defined as the change in length relative to the adjusted gauge length, divided by the adjusted gauge length, multiplied by 100.
   b. Pre-strain loading: Pull the specimen to the 500% strain at a constant cross head speed of 508 mm/min (10 in/min). Report the load at 200% as $F200_{PS}$ in (N/in)
   c. Pre-strain unloading: Return the crosshead to original gage length of 25.4 mm at a constant cross head speed of 508 mm/min.
   d. Open the bottom grip and hold the specimen in the unstrained state for 1 minute.
   e. Regrip the sample as described above with minimum slack and minimum load.
   f. Repeat the pre-load step, and define new adjusted gauge length ($l_{ini}$), and use it to calculate strain % for the first and second cycle.
   g. First cycle loading: Pull the specimen to the 200% strain at a constant cross head speed of 508 mm/min. Report the load at 200% as $F200_{FC}$ in (N/in)
   h. First cycle unload: Next, hold the specimen at the 200% strain for 30 seconds and then return the crosshead to its starting position (i.e. 0% strain) at a constant cross head speed of 508 mm/min.
   i. Second cycle: Hold sample at 0% strain for 30 seconds, and re-run first cycle as described in steps "e" and "f" above.

A computer data system records the Load (force) exerted on the sample during the test as a function of applied strain. From the resulting data generated, the $F200_{PS}$ and $F200_{FC}$ are reported. The testing is repeated for at least 3 separate samples and the average is reported as the Average $F200_{PS}$ and the Average $F200_{FC}$ respectively, along with standard deviation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling elastic laminates, the method comprising the steps of:
    providing a first substrate and a second substrate, the first substrate and the second substrate each comprising a first surface and an opposing second surface, and defining a width in a cross direction;
    wrapping the first surface of the first substrate onto an outer circumferential surface of an anvil;
    advancing an elastic film to a spreader mechanism, the spreader mechanism comprising an engagement portion and the elastic film;
    stretching the elastic film at the spreader mechanism in the cross direction to a first elongation;
    advancing the elastic film from the spreader mechanism to the anvil, wherein the anvil comprises an active vacuum zone having a maximum width in the cross direction (Wv), wherein the maximum width is divided into a first portion and a second portion, wherein the first portion is disposed in overlapping relationship with the engagement portion and inboard of the engagement portion in the cross direction and the first portion has a first width in the cross direction (VZi) and wherein the second portion has a second width in the cross direction (VZo), and wherein the first width in the cross direction (VZi) is greater than the second width in the cross direction (VZo);
    positioning the elastic film in contact with the second surface of the first substrate on the anvil;
    advancing the second substrate to position the first surface of the second substrate in contact with the elastic film and the second surface of the first substrate on the anvil; and
    ultrasonically bonding the first substrate together with the second substrate with the elastic film positioned between the first substrate and the second substrate.

2. The method of claim 1 wherein the engagement portion comprises one or more radially protruding nubs.

3. The method of claim 1 wherein the anvil comprises a plurality of apertures fluidly connected with a vacuum source in the active vacuum zone.

4. The method of claim 1 wherein the anvil comprises a maximum width (Wa) in the cross direction and wherein the maximum width of the active vacuum zone in the cross direction (Wv) is less than the maximum width of the anvil (Wa).

5. The method of claim 4 wherein the maximum width of the active vacuum zone in the cross direction (Wv) is about 20% or less of the maximum width of the anvil (Wa).

6. The method of claim 1 further comprising the step of:
    providing one or more reinforcement layers between the elastic film and the first substrate and/or the second substrate.

7. The method of claim 6 wherein the step of providing the one or more reinforcement layers comprises folding a section of the first substrate to position a first longitudinal edge of the first substrate between the second surface of the first substrate and the elastic film.

8. The method of claim 1 wherein a ratio of the first width in the cross direction (VZi) to the second width in the cross direction (VZo) is greater than 5.

9. The method of claim 1 wherein the anvil comprises a second active vacuum zone separated from the active vacuum zone by a distance in the cross direction (DS) that is at least 60% of a maximum width of the anvil (Wa).

10. The method of claim 1 wherein the anvil comprises a configurable tube in fluid communication with an outer surface of the anvil through radially extending connectors; the method further using the configurable tube to provide the active vacuum zone.

11. The method of claim 1 wherein the anvil comprises a configurable tube designed to be removable from the anvil.

12. The method of claim 11 wherein the configurable tube comprises ports that are fluidly connected to a vacuum source and also fluidly connected through radially extending connectors to the outer circumferential surface of the anvil.

13. The method of claim 11 wherein the configurable tube comprises a plurality of blocking mechanisms configured to direct vacuum pressure to the active vacuum zone of the anvil.

14. The method of claim 13 wherein the plurality of blocking mechanisms are disposed on the configurable tube and are configured to define one lane on the outer circumferential surface of the anvil.

15. The method of claim 13 wherein the plurality of blocking mechanisms are disposed on the configurable tube and are configured to define multiple lanes on the outer circumferential surface of the anvil.

16. The method of claim 1 wherein the anvil is configured to accept a plurality of configurable tubes, each configurable tube of the plurality of configurable tubes comprises a different configuration of vacuum porting to activate and/or inactivate alternate operative vacuum apertures in the outer circumferential surface of the anvil.

17. The method of claim 16 wherein a first configurable tube of the plurality of configurable tubes comprises a configuration of vacuum porting designed to define a single lane on the outer circumferential surface of the anvil.

18. The method of claim 16 wherein a second configurable tube of the plurality of configurable tubes comprises a configuration of vacuum porting designed to define more than one lane on the outer circumferential surface of the anvil.

* * * * *